United States Patent
Meyers et al.

(10) Patent No.: US 8,268,006 B2
(45) Date of Patent: Sep. 18, 2012

(54) CONSTRAINED PROSTHETIC KNEE WITH ROTATING BEARING

(75) Inventors: John E. Meyers, Columbia City, IN (US); G. Doug Letson, Tampa, FL (US); Russell Windsor, Larchmont, NY (US); Vincent A. Webster, Warsaw, IN (US); Bill N. Sisk, Claypool, IN (US); Bill H. Haywood, Warsaw, IN (US); Adam M. Griner, Columbia City, IN (US); Michael Cook, Claypool, IN (US); Rodney L. Bays, Pierceton, IN (US); Jerry L. Aikins, Warsaw, IN (US); Marvin Figueroa, Warsaw, IN (US); Peter S. Walker, New York, NY (US)

(73) Assignee: Zimmer, Inc., Warsaw, IN (US)

(*) Notice: Subject to any disclaimer, the term of this patent is extended or adjusted under 35 U.S.C. 154(b) by 0 days.

(21) Appl. No.: 12/790,181

(22) Filed: May 28, 2010

(65) Prior Publication Data
US 2010/0234962 A1 Sep. 16, 2010

Related U.S. Application Data

(63) Continuation of application No. 11/956,998, filed on Dec. 14, 2007, now abandoned, which is a continuation of application No. 10/805,056, filed on Mar. 19, 2004, now abandoned, which is a continuation of application No. 10/001,000, filed on Nov. 2, 2001, now Pat. No. 6,719,800, which is a continuation-in-part of application No. 09/771,061, filed on Jan. 29, 2001, now Pat. No. 6,485,519.

(51) Int. Cl.
*A61F 2/38* (2006.01)

(52) U.S. Cl. .................................................. 623/20.29

(58) Field of Classification Search .... 623/20.14–20.35, 623/19.11, 19.12, 19.13, 19.14, 20.11, 20.12, 623/20.13
See application file for complete search history.

(56) References Cited

U.S. PATENT DOCUMENTS
3,696,446 A 10/1972 Bousquet et al.
(Continued)

FOREIGN PATENT DOCUMENTS
BR 7506468 A 12/1975
(Continued)

OTHER PUBLICATIONS

European Search Report issued Feb. 3, 2006 in related European Application No. EP04012041.2.
(Continued)

*Primary Examiner* — Alvin J. Stewart
(74) *Attorney, Agent, or Firm* — Schwegman Lundberg & Woessner, P.A.

(57) ABSTRACT

A constrained prosthetic knee having a modular hinge post and a rotating bearing. A cannulated hinge post is rotatably connected to the femoral component of the knee prosthesis so that a hinge post extension may be anteriorly positioned through the hinge post and into the tibial component of the knee prosthesis, after positioning of the femoral component in the femur and the tibial component in the tibia. The hinge post is preassembled to the femoral component so that such assembly is not required during the implantation procedure. A meniscal component forming the rotating bearing of the knee prosthesis is packaged together with the hinge post extension so that the appropriate hinge post extension is readily available. The meniscal component includes a mechanism for preventing lift off of the meniscal component from the tibial component, while allowing rotation of the meniscal component relative to the tibial component.

25 Claims, 12 Drawing Sheets

U.S. PATENT DOCUMENTS

| | | | |
|---|---|---|---|
| 3,708,805 A | 1/1973 | Scales et al. | |
| 3,813,700 A | 6/1974 | Tavernetti et al. | |
| 3,816,853 A | 6/1974 | Elson | |
| 3,824,630 A | 7/1974 | Johnston | |
| 3,837,009 A | 9/1974 | Walker | |
| 3,869,729 A | 3/1975 | Attenborouch | |
| 3,918,101 A | 11/1975 | LaGrange et al. | |
| 3,924,277 A | 12/1975 | Freeman et al. | |
| 3,934,272 A | 1/1976 | Wearne et al. | |
| 3,996,624 A | 12/1976 | Noiles | |
| 4,016,606 A | 4/1977 | Murray et al. | |
| 4,064,568 A | 12/1977 | Grundei et al. | |
| 4,092,740 A | 6/1978 | Eshriqui | |
| 4,112,522 A | 9/1978 | Dadurian et al. | |
| 4,134,158 A | 1/1979 | Laure | |
| 4,136,405 A | 1/1979 | Patrick et al. | |
| 4,219,893 A | 9/1980 | Noiles | |
| 4,224,697 A | 9/1980 | Murray | |
| 4,257,129 A | 3/1981 | Volz | |
| 4,262,368 A | 4/1981 | Lacey | |
| 4,268,920 A | 5/1981 | Engelbrecht | |
| 4,301,553 A | 11/1981 | Noiles | |
| 4,340,978 A | 7/1982 | Buechel et al. | |
| 4,358,859 A | 11/1982 | Schurman et al. | |
| 4,383,337 A | 5/1983 | Volz et al. | |
| 4,404,691 A | 9/1983 | Buning | |
| 4,462,120 A | 7/1984 | Rambert et al. | |
| 4,538,305 A | 9/1985 | Engelbrecht | |
| 4,578,081 A | 3/1986 | Harder et al. | |
| 4,655,778 A | 4/1987 | Koeneman | |
| 4,662,889 A | 5/1987 | Zichner et al. | |
| 4,764,171 A | 8/1988 | Harder et al. | |
| 4,790,853 A | 12/1988 | Engelbrecht et al. | |
| 4,790,854 A | 12/1988 | Harder et al. | |
| 4,822,366 A | 4/1989 | Bolesky | |
| 4,828,564 A | 5/1989 | Scales et al. | |
| 4,834,758 A | 5/1989 | Lane et al. | |
| 4,865,606 A | 9/1989 | Rehder | |
| 4,888,021 A | 12/1989 | Forte et al. | |
| 4,919,660 A | 4/1990 | Peilloud | |
| 4,923,472 A | 5/1990 | Ugolini | |
| 4,936,853 A * | 6/1990 | Fabian et al. | 623/20.15 |
| 4,938,769 A * | 7/1990 | Shaw | 623/20.15 |
| 4,944,757 A * | 7/1990 | Martinez et al. | 623/20.15 |
| 4,950,298 A * | 8/1990 | Gustilo et al. | 623/20.15 |
| 5,007,933 A | 4/1991 | Sidebotham et al. | |
| 5,011,496 A | 4/1991 | Forte et al. | |
| 5,015,255 A | 5/1991 | Kuslich | |
| 5,019,103 A | 5/1991 | Van Zile et al. | |
| 5,037,439 A | 8/1991 | Albrektsson et al. | |
| 5,061,271 A | 10/1991 | Van Zile | |
| 5,116,375 A | 5/1992 | Hoffman | |
| 5,123,928 A | 6/1992 | Moser | |
| 5,139,521 A | 8/1992 | Schelhas | |
| 5,171,283 A * | 12/1992 | Pappas et al. | 623/20.29 |
| 5,180,383 A | 1/1993 | Haydon | |
| 5,194,066 A * | 3/1993 | Van Zile | 623/20.15 |
| 5,246,459 A | 9/1993 | Elias et al. | |
| 5,282,867 A | 2/1994 | Mikhail | |
| 5,290,313 A * | 3/1994 | Heldreth | 623/20.15 |
| 5,314,481 A | 5/1994 | Bianco | |
| 5,326,368 A | 7/1994 | Collazo | |
| 5,330,534 A | 7/1994 | Herrington et al. | |
| 5,358,527 A | 10/1994 | Forte | |
| 5,370,700 A | 12/1994 | Sarkisian et al. | |
| 5,370,701 A * | 12/1994 | Finn | 623/20.25 |
| 5,387,240 A * | 2/1995 | Pottenger et al. | 623/20.29 |
| 5,395,401 A * | 3/1995 | Bahler | 623/20.29 |
| 5,405,398 A | 4/1995 | Buford, III et al. | |
| 5,411,555 A | 5/1995 | Nieder | |
| 5,413,607 A | 5/1995 | Engelbrecht et al. | |
| 5,427,586 A | 6/1995 | Schelhas | |
| 5,458,644 A | 10/1995 | Grundei | |
| 5,489,307 A | 2/1996 | Kuslich et al. | |
| 5,489,311 A | 2/1996 | Cipolletti | |
| 5,549,687 A | 8/1996 | Coates et al. | |
| 5,549,689 A | 8/1996 | Epstein et al. | |
| 5,609,639 A * | 3/1997 | Walker | 623/20.29 |
| 5,609,643 A * | 3/1997 | Colleran et al. | 623/20.29 |
| 5,658,342 A * | 8/1997 | Draganich et al. | 623/20.29 |
| 5,683,468 A * | 11/1997 | Pappas | 623/20.29 |
| 5,702,458 A | 12/1997 | Burstein et al. | |
| 5,702,466 A * | 12/1997 | Pappas et al. | 623/20.29 |
| 5,725,580 A | 3/1998 | Cloutier et al. | |
| 5,755,804 A * | 5/1998 | Schmotzer et al. | 623/20.24 |
| 5,766,257 A | 6/1998 | Goodman et al. | |
| 5,772,661 A | 6/1998 | Michelson | |
| 5,776,200 A * | 7/1998 | Johnson et al. | 623/20.15 |
| 5,776,201 A | 7/1998 | Colleran et al. | |
| 5,800,552 A * | 9/1998 | Forte | 623/20.27 |
| 5,824,096 A * | 10/1998 | Pappas et al. | 623/23.39 |
| 5,824,102 A | 10/1998 | Buscayret | |
| 5,879,392 A | 3/1999 | McMinn | |
| 5,879,394 A | 3/1999 | Ashby et al. | |
| 5,906,643 A * | 5/1999 | Walker | 623/20.29 |
| 5,954,770 A * | 9/1999 | Schmotzer et al. | 623/20.24 |
| 5,964,808 A | 10/1999 | Blaha et al. | |
| 6,004,352 A | 12/1999 | Buni | |
| 6,013,103 A * | 1/2000 | Kaufman et al. | 623/20.15 |
| 6,019,794 A | 2/2000 | Walker | |
| 6,080,195 A | 6/2000 | Colleran et al. | |
| 6,099,570 A * | 8/2000 | Livet et al. | 623/20.21 |
| 6,099,571 A | 8/2000 | Knapp | |
| 6,117,175 A | 9/2000 | Bosredon | |
| 6,126,692 A * | 10/2000 | Robie et al. | 623/20.32 |
| 6,143,034 A * | 11/2000 | Burrows | 623/20.29 |
| 6,162,255 A * | 12/2000 | Oyola | 623/20.34 |
| 6,171,342 B1 | 1/2001 | O'Neil | |
| 6,264,696 B1 | 7/2001 | Reigner et al. | |
| 6,267,763 B1 | 7/2001 | Castro | |
| 6,296,666 B1 * | 10/2001 | Gardner | 623/20.29 |
| 6,299,646 B1 | 10/2001 | Chambat et al. | |
| 6,306,171 B1 | 10/2001 | Conzemius | |
| 6,306,172 B1 * | 10/2001 | O'Neil | 623/20.15 |
| 6,319,283 B1 * | 11/2001 | Insall et al. | 623/20.33 |
| 6,361,564 B1 * | 3/2002 | Marceaux et al. | 623/20.29 |
| 6,428,577 B1 * | 8/2002 | Evans et al. | 623/20.29 |
| 6,436,145 B1 * | 8/2002 | Miller | 623/20.34 |
| 6,443,991 B1 | 9/2002 | Running | |
| 6,447,549 B1 * | 9/2002 | Taft | 623/20.15 |
| 6,485,519 B2 * | 11/2002 | Meyers et al. | 623/20.24 |
| 6,491,726 B2 * | 12/2002 | Pappas | 623/20.29 |
| 6,500,208 B1 * | 12/2002 | Metzger et al. | 623/20.28 |
| 6,506,215 B1 * | 1/2003 | Letot et al. | 623/20.29 |
| 6,620,198 B2 * | 9/2003 | Burstein et al. | 623/20.28 |
| 6,629,999 B1 * | 10/2003 | Serafin, Jr. | 623/20.15 |
| 6,652,588 B2 | 11/2003 | Hayes et al. | |
| 6,719,800 B2 * | 4/2004 | Meyers et al. | 623/20.24 |
| 6,743,258 B1 * | 6/2004 | Keller | 623/20.14 |
| 6,755,864 B1 * | 6/2004 | Brack et al. | 623/20.29 |
| 6,770,097 B2 | 8/2004 | Leclercq | |
| 6,773,461 B2 * | 8/2004 | Meyers et al. | 623/20.24 |
| 6,984,249 B2 | 1/2006 | Keller | |
| 7,070,622 B1 * | 7/2006 | Brown et al. | 623/20.14 |
| 7,172,628 B2 | 2/2007 | Lamprich et al. | |
| 7,175,665 B2 * | 2/2007 | German et al. | 623/20.15 |
| 7,232,465 B2 * | 6/2007 | Keller | 623/20.24 |
| 7,326,252 B2 * | 2/2008 | Otto et al. | 623/20.15 |
| 7,357,817 B2 * | 4/2008 | D'Alessio, II | 623/20.15 |
| 7,569,054 B2 | 8/2009 | Michelson | |
| 7,572,292 B2 * | 8/2009 | Crabtree et al. | 623/20.24 |
| 7,591,855 B2 | 9/2009 | Keller | |
| 7,658,767 B2 * | 2/2010 | Wyss | 623/20.29 |
| 7,753,960 B2 * | 7/2010 | Cipolletti et al. | 623/20.29 |
| 7,871,442 B2 * | 1/2011 | Servidio | 623/20.27 |
| 2001/0003803 A1 * | 6/2001 | Leclercq | 623/20.29 |
| 2001/0025199 A1 | 9/2001 | Rauscher | |
| 2001/0034554 A1 * | 10/2001 | Pappas | 623/20.29 |
| 2002/0103541 A1 | 8/2002 | Meyers et al. | 623/20.24 |
| 2002/0107576 A1 | 8/2002 | Meyers et al. | 623/20.24 |
| 2002/0161448 A1 | 10/2002 | Hayes et al. | |
| 2003/0009228 A1 * | 1/2003 | Meyers et al. | 623/20.24 |
| 2003/0009232 A1 * | 1/2003 | Metzger et al. | 623/20.29 |
| 2003/0153980 A1 * | 8/2003 | Brack | 623/20.33 |
| 2004/0054416 A1 * | 3/2004 | Wyss et al. | 623/20.27 |
| 2004/0162620 A1 * | 8/2004 | Wyss | 623/20.27 |
| 2004/0186583 A1 | 9/2004 | Keller | |

| | | | | | | | |
|---|---|---|---|---|---|---|---|
| 2004/0186584 | A1* | 9/2004 | Keller ............... 623/20.24 | FR | 2641966 | A1 | 7/1990 |
| 2004/0220676 | A1* | 11/2004 | Keller ............... 623/20.31 | FR | 2692475 | A1 | 12/1993 |
| 2004/0249467 | A1* | 12/2004 | Meyers et al. ....... 623/20.24 | FR | 2696926 | A1 | 4/1994 |
| 2005/0107886 | A1* | 5/2005 | Crabtree et al. ..... 623/20.24 | FR | 2702651 | A1 | 9/1994 |
| 2005/0192672 | A1* | 9/2005 | Wyss et al. .......... 623/20.27 | FR | 2711750 | A1 | 5/1995 |
| 2005/0246028 | A1* | 11/2005 | Pappas et al. ........ 623/20.25 | FR | 2751204 | A1 | 1/1998 |
| 2007/0100463 | A1* | 5/2007 | Aram et al. .......... 623/20.29 | FR | 2760352 | A1 | 9/1998 |
| 2008/0004708 | A1* | 1/2008 | Wyss ................... 623/20.24 | FR | 2771283 | A1 | 5/1999 |
| 2008/0097616 | A1* | 4/2008 | Meyers et al. ....... 623/20.29 | FR | 2777453 | A1 | 10/1999 |
| 2008/0167722 | A1* | 7/2008 | Metzger et al. ...... 623/20.36 | FR | 2787992 | A1 | 7/2000 |
| 2008/0255671 | A1* | 10/2008 | Kriek .................. 623/20.29 | FR | 2793676 | A1 | 11/2000 |
| 2009/0024221 | A1* | 1/2009 | Ball ..................... 623/20.11 | FR | 2793677 | A1 | 11/2000 |
| 2009/0082873 | A1* | 3/2009 | Hazebrouck et al. . 623/20.32 | GB | 1409150 | A | 10/1975 |
| 2009/0088860 | A1* | 4/2009 | Romeis et al. ....... 623/20.24 | GB | 1507309 | A | 4/1978 |
| 2009/0125116 | A1* | 5/2009 | Crabtree et al. ..... 623/20.24 | GB | 1514479 | A | 6/1978 |
| 2009/0149964 | A1* | 6/2009 | May et al. ............ 623/20.15 | GB | 2070939 | A | 9/1981 |
| 2009/0299482 | A1* | 12/2009 | Metzger et al. ...... 623/20.29 | GB | 2129306 | A | 5/1984 |
| 2009/0326665 | A1* | 12/2009 | Wyss et al. .......... 623/20.21 | JP | 8-173464 | A | 7/1996 |
| 2009/0326666 | A1* | 12/2009 | Wyss et al. .......... 623/20.29 | JP | 10-014935 | A | 1/1998 |
| 2010/0016978 | A1* | 1/2010 | Williams et al. ..... 623/20.27 | RU | 2080840 | C1 | 6/1997 |
| 2010/0016980 | A1* | 1/2010 | Donno et al. ........ 623/20.32 | WO | WO94/21198 | A1 | 9/1994 |
| 2010/0042224 | A1* | 2/2010 | Otto et al. ............ 623/20.27 | WO | WO00/66043 | A1 | 11/2000 |
| 2010/0063594 | A1* | 3/2010 | Hazebrouck et al. . 623/20.29 | | | | |
| 2010/0100189 | A1* | 4/2010 | Metzger ............... 623/20.14 | | | | |
| 2010/0234962 | A1* | 9/2010 | Meyers et al. ....... 623/20.29 | | | | |

FOREIGN PATENT DOCUMENTS

| | | |
|---|---|---|
| CA | 1073151 A | 3/1980 |
| DE | 2122390 A1 | 1/1973 |
| DE | 2154338 A1 | 5/1973 |
| DE | 2244064 A1 | 3/1974 |
| DE | 2334265 A1 | 1/1975 |
| DE | 2543911 A1 | 4/1976 |
| DE | 2545821 A1 | 4/1976 |
| DE | 2539717 A1 | 3/1977 |
| DE | 2810748 A1 | 11/1978 |
| DE | 2744710 A1 | 4/1979 |
| DE | 3022668 A1 | 12/1981 |
| DE | 3529894 A1 | 3/1987 |
| DE | 4102509 A1 | 7/1992 |
| DE | 4110048 C1 | 7/1992 |
| DE | 9414970 U1 | 12/1994 |
| DE | 4434806 A1 | 4/1996 |
| DE | 69206397 T2 | 8/1996 |
| DE | 69305434 T2 | 11/1997 |
| DE | 19809041 A1 | 9/1999 |
| DE | 19915053 A1 | 10/1999 |
| DE | 69324016 T2 | 10/1999 |
| DE | 10012059 A1 | 9/2001 |
| DE | 69712258 T2 | 3/2003 |
| EP | 0046926 A2 | 3/1982 |
| EP | 0069683 A1 | 1/1983 |
| EP | 0083155 A1 | 7/1983 |
| EP | 0126978 A1 | 12/1984 |
| EP | 0177755 A1 | 4/1986 |
| EP | 0178445 A1 | 4/1986 |
| EP | 0194326 A1 | 9/1986 |
| EP | 0198163 A2 | 10/1986 |
| EP | 0214773 A2 | 3/1987 |
| EP | 0265325 A1 | 4/1988 |
| EP | 017755 B1 | 11/1988 |
| EP | 0177755 B1 | 11/1988 |
| EP | 0410237 A1 | 1/1991 |
| EP | 0420460 A1 | 4/1991 |
| EP | 0472475 A2 | 2/1992 |
| EP | 0716839 A1 | 6/1996 |
| EP | 0724868 A1 | 8/1996 |
| EP | 0812582 A2 | 12/1997 |
| EP | 0653194 B1 | 3/1999 |
| EP | 0923916 A1 | 6/1999 |
| EP | 1108403 A1 | 6/2001 |
| EP | 1132064 A2 | 9/2001 |
| EP | 1226800 A2 | 7/2002 |
| EP | 1417938 A1 | 5/2004 |
| EP | 1447060 A2 | 8/2004 |
| EP | 1447060 A3 | 3/2006 |
| FR | 2601873 A1 | 1/1988 |
| FR | 2612767 A1 | 9/1988 |
| FR | 2628316 A1 | 9/1989 |

OTHER PUBLICATIONS

European Office Action mailed Jul. 3, 2007 in related European Application No. EP04012041.2.
European Office Action mailed Sep. 26, 2007 in related European Application No. EP03255512.0.
Canadian Office Action mailed Mar. 2, 2009 in related Canadian Application No. 2,367,652.
Response filed Sep. 2, 2009 to the Canadian Office Action mailed Mar. 2, 2009 in related Canadian Application No. 2,367,652.
Office Action mailed Dec. 2, 2010 in related U.S. Appl. No. 12/776,218.
Office Action mailed Nov. 19, 2010 in related U.S. Appl. No. 12/776,221.
Office Action mailed Nov. 19, 2010 in related U.S. Appl. No. 12/776,224.
European Search Report included in EP 1 417 938 A1 published by the European Patent Office on Dec. 5, 2004 on European Application No. 03255512.0, which claims priority from related U.S. Appl. No. 10/234,362, now U.S. Patent No. 6,773,461.
European Search Report EP 1 447 060 A3 issued by the European Patent Office on Mar. 22, 2006 on European Application No. 04012041.2, which claims priority from related U.S. Appl. No. 09/771,061, now U.S. Patent No. 6,485,519.
Amendment filed Apr. 4, 2011 in related U.S. Appl. No. 12/776,218.
Amendment filed Apr. 4, 2011 in related U.S. Appl. No. 12/776,221.
Amendment filed Apr. 4, 2011 in related U.S. Appl. No. 12/776,224.
Office Action mailed Dec. 11, 2009 in related U.S. Appl. No. 11/956,998.
Office Action mailed Apr. 18, 2011 in related U.S. Appl. No. 12/776,218.
Office Action mailed Apr. 18, 2011 in related U.S. Appl. No. 12/776,221.
Office Action mailed Apr. 19, 2011 in related U.S. Appl. No. 12/776,224.
Office Action mailed Sep. 8, 2011 in related U.S. Appl. No. 12/776,218.
Office Action mailed Oct. 28, 2011 in related U.S. Appl. No. 12/776,221.
Office Action mailed Sep. 7, 2011 in related U.S. Appl. No. 12/776,224.
Amendment filed Aug. 18, 2011 in related U.S. Appl. No. 12/776,218.
Amendment filed Oct. 18, 2011 in related U.S. Appl. No. 12/776,221.
Amendment filed Aug. 19, 2011 in related U.S. Appl. No. 12/776,224.
European office action mailed Nov. 2, 2010 in European Patent Application No. 02250512.7.
European Search Report completed Dec. 10, 2010 in European Patent Application No. 10012582.2.
European Search Report completed Dec. 13, 2010 in European Patent Application No. 10012581.4.

Response to Search Opinion of Dec. 20, 2010 filed in theEuropean Patent Office on May 12, 2011 in European Patent Application No. 10012582.2.
Amendment filed Sep. 30, 2010 in the European Patent Office in European Patent Application No. 02250512.7.
Amendment filed Mar. 8, 2012 in related U.S. Appl. No. 12/776,218.
Amendment filed Mar. 28, 2012 in related U.S. Appl. No. 12/776,221.
Amendment filed Mar. 7, 2012 in related U.S. Appl. No. 12/776,224.
Office Action mailed May 2, 2003 in related U.S. Appl. No. 10/001,000.
Amendment filed Jul. 25, 2003 in related U.S. Appl. No. 10/001,000.
Final Office Action mailed Apr. 24, 2012 in related U.S. Appl. No. 12/776,218.
Final Office Action mailed Apr. 24, 2012 in related U.S. Appl. No. 12/776,221.
Final Office Action mailed Apr. 24, 2012 in related U.S. Appl. No. 12/776,224.
Supplemental Amendment filed Mar. 9, 2012 in related U.S. Appl. No. 12/776,224.

* cited by examiner

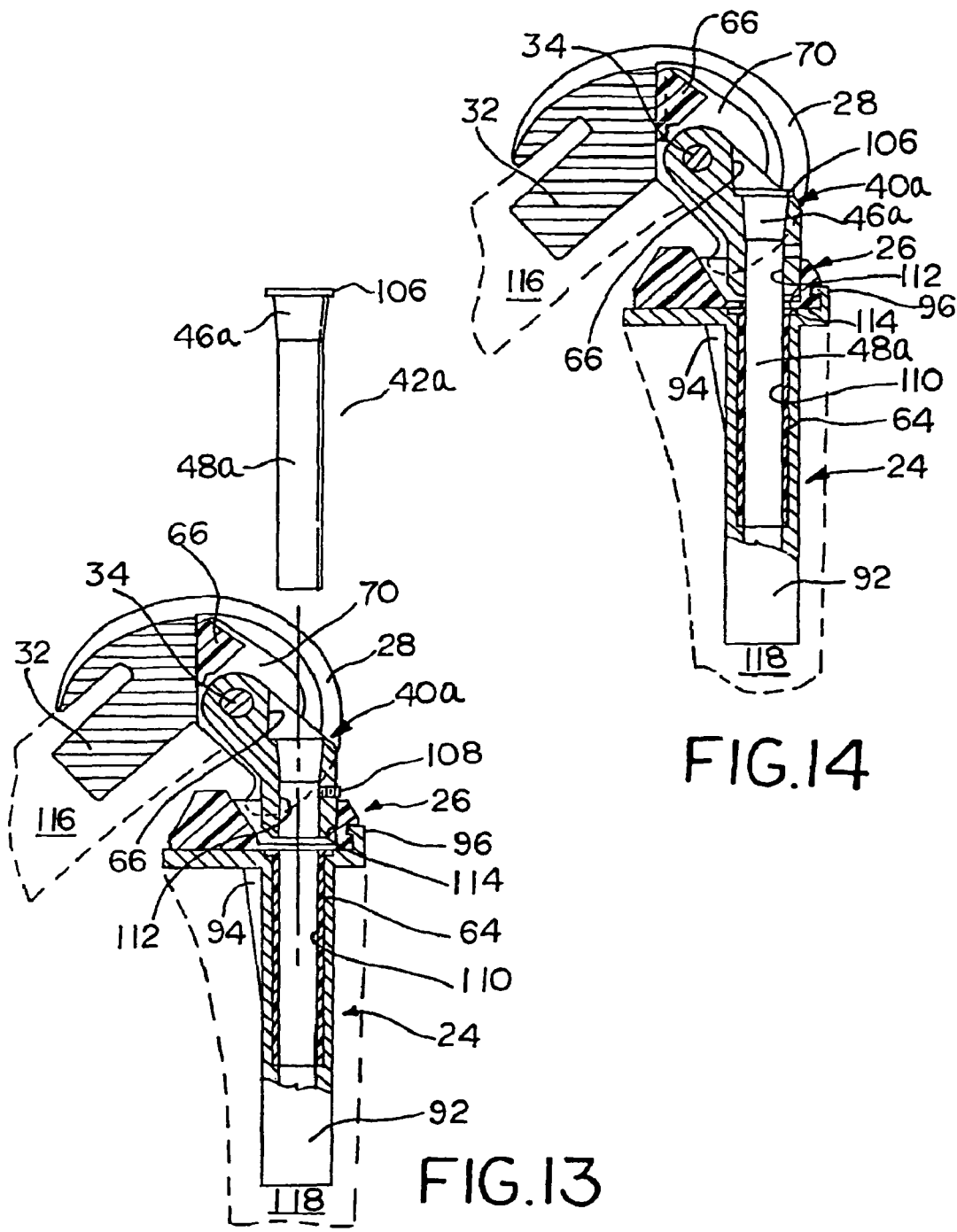

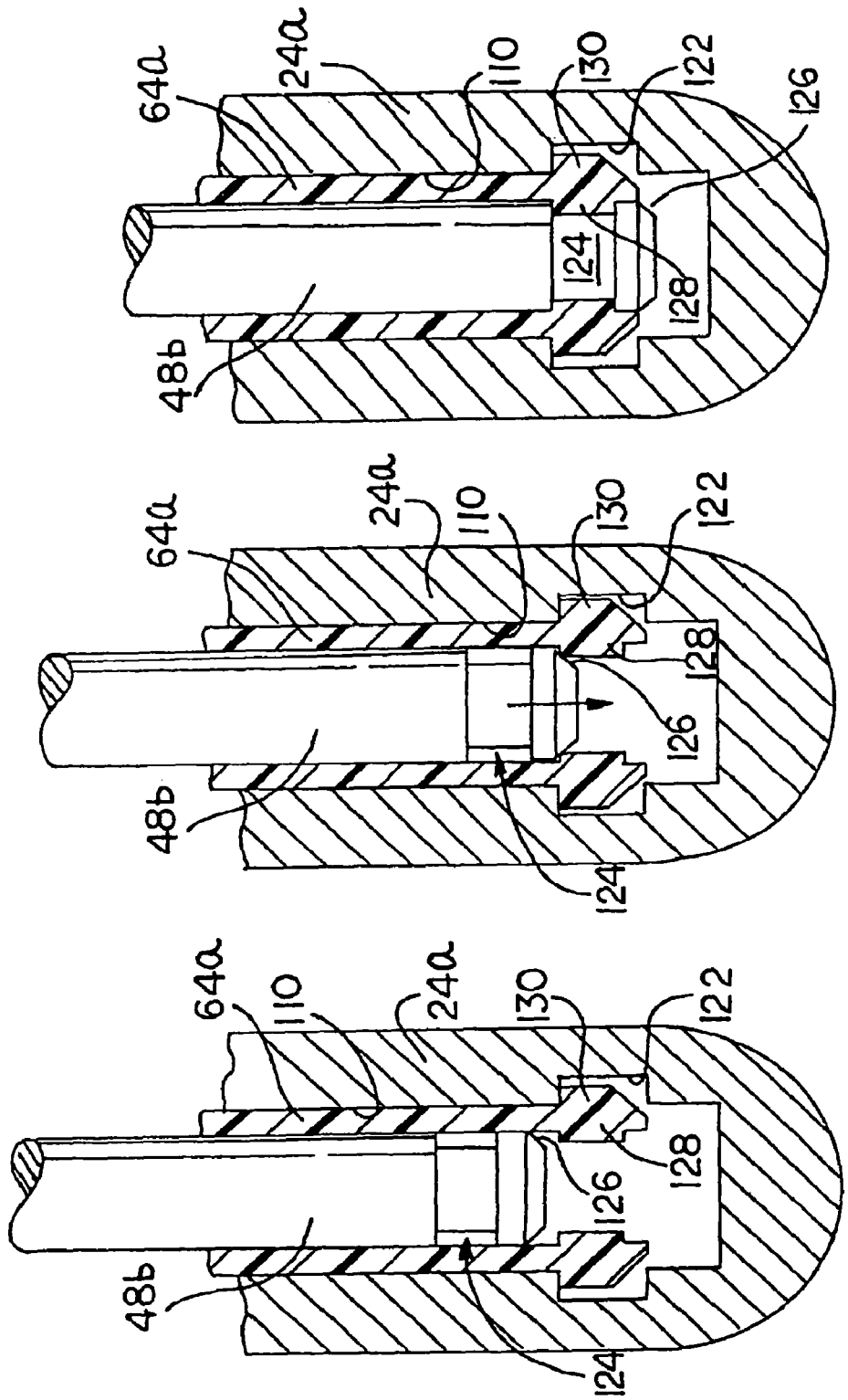

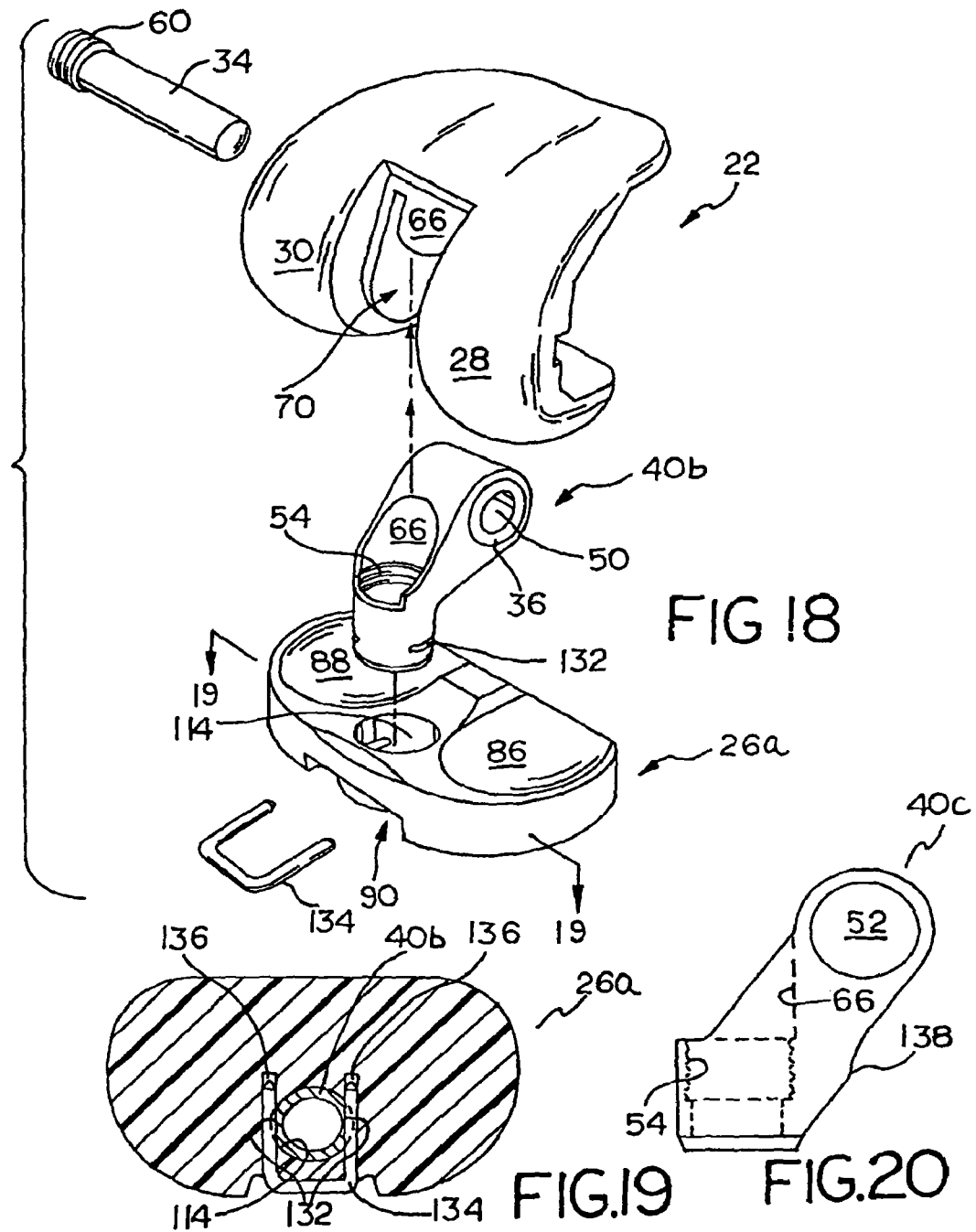

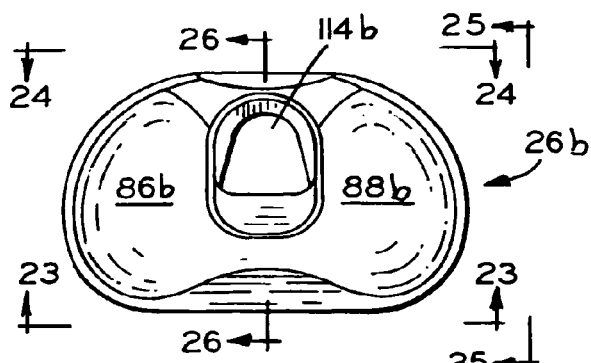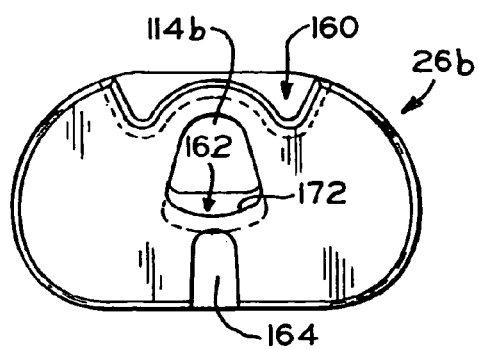
FIG.21  FIG.22
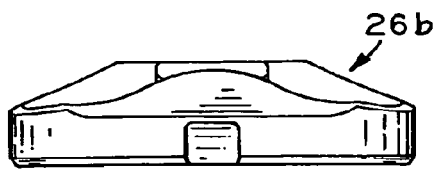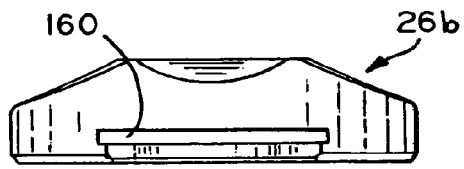
FIG.23  FIG.24
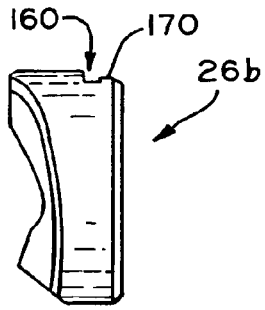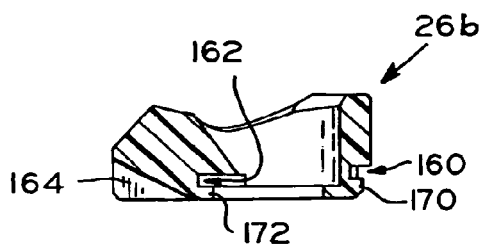
FIG.25  FIG.26

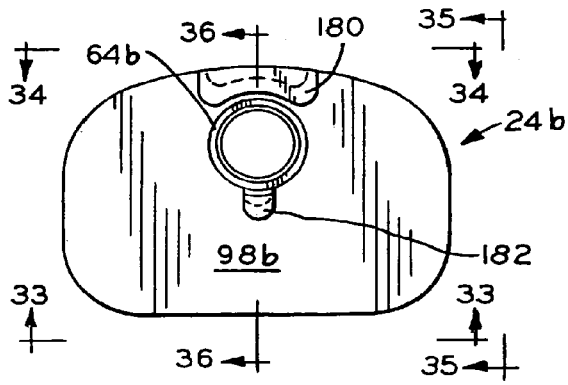
FIG._31
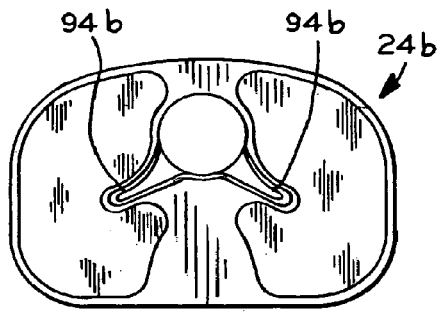
FIG._32
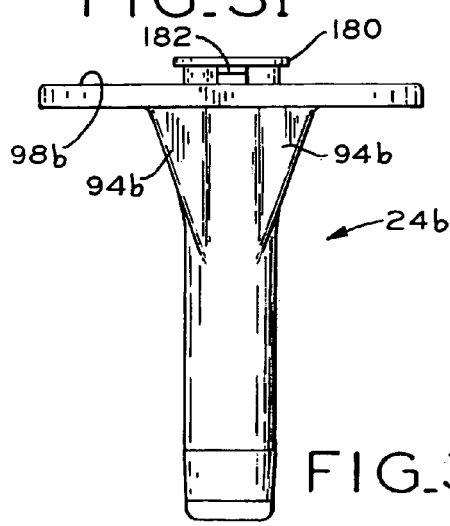
FIG.33
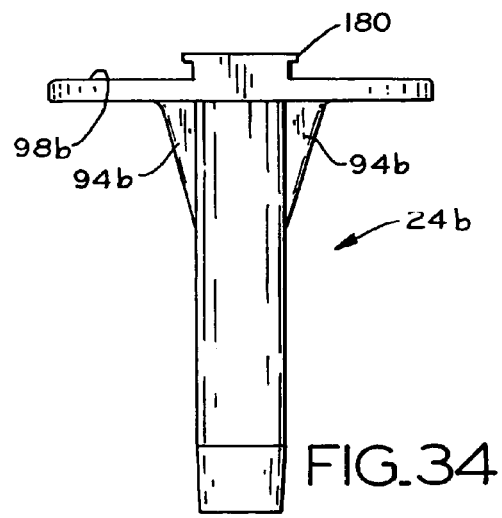
FIG.34
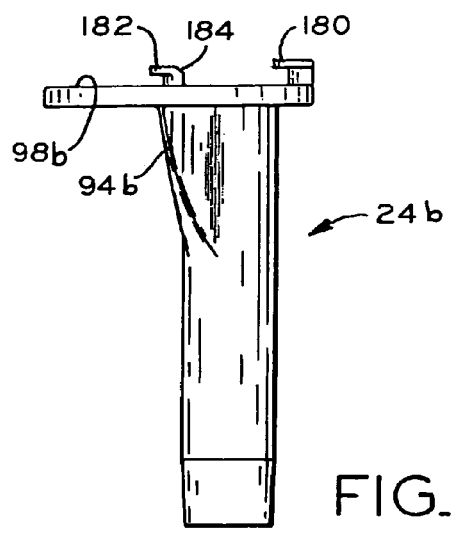
FIG.35
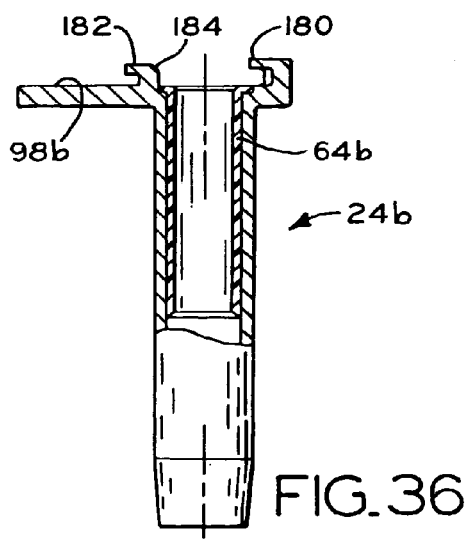
FIG.36

CONSTRAINED PROSTHETIC KNEE WITH ROTATING BEARING

CROSS-REFERENCE TO RELATED APPLICATIONS

This application is a continuation of U.S. patent application Ser. No. 11/956,998, entitled CONSTRAINED PROSTHETIC KNEE WITH ROTATING BEARING, filed on Dec. 14, 2007, which is a continuation of U.S. patent application Ser. No. 10/805,056 filed Mar. 19, 2004, now abandoned, which is a continuation of U.S. patent application Ser. No. 10/001,000 filed Nov. 2, 2001, now U.S. Pat. No. 6,719,800, which is a continuation-in-part of U.S. patent application Ser. No. 09/771,061 filed Jan. 29, 2001, now U.S. Pat. No. 6,485,519, the entire disclosures of which are hereby expressly incorporated herein by reference.

BACKGROUND OF THE INVENTION

1. Field of the Invention

The present invention relates to prosthetic joints, and, more particularly to a constrained prosthetic knee having a modular hinge post and a rotating bearing.

2. Description of the Related Art

Generally, the knee is formed by the pair of condyles at the distal portion of the femur, the lower surfaces of which bear upon the correspondingly shaped proximal surface plateau of the tibia. The femur and tibia are connected by means of ligaments such as, the posterior cruciate ligament, the lateral collateral ligament, the medial collateral ligament, and the anterior cruciate ligament. These ligaments provide stability to the joint formed by the femur and tibia (i.e., the knee).

In a broad sense, prosthetic knee joints can be considered either constrained or unconstrained. For the purposes of this discussion, constrained prosthetic knees include femoral and tibial prosthetic components which are mechanically linked or constrained to each other by a hinge structure. An unconstrained prosthetic knee includes femoral and tibial components which are not mechanically linked. An unconstrained knee utilizes the patient's existing ligaments to provide joint stability. With this in mind, constrained prosthetic knees have particular applicability to cases in which a patient has experienced ligament loss and/or the existing ligaments do not provide adequate support and stability to the knee.

Tibial components of a prosthetic knee can be formed as a one-piece configuration in which the tibial tray forms the meniscal component of the prosthetic knee. Various other prosthetic knees utilize a modular meniscal component separate from the tibial component. Devices utilizing modular meniscal components include those in which the meniscal component (i.e., tibial bearing surface) is fixed to the tibial tray portion of the tibial component and is incapable of movement relative thereto. Alternative devices utilize a modular meniscal component capable of movement relative to the tibial tray. Devices in which relative rotational movement occurs between the meniscal component and the tibial component are typically referred to as rotating bearing knees. Rotating bearing knees thus allow movement between the bearing (i.e., meniscal component) and the tibial tray, as well as movement between the femoral component and the tibial bearing.

Constrained knees of the prior art include constructions in which a hinge post extension is first positioned within a tibial component (with an end protruding therefrom) and is thereafter connected to the femoral component by positioning the hinge post (rotatably attached to the femoral component) over the top of the protruding end of the hinge post extension and thereafter connecting the hinge post extension to the hinge post, e.g., by threading the hinge post extension into the hinge post. After making this connection, the meniscal component is thereafter slid into position between the femoral component and the tibial component. Meniscal components utilized with these prior art prosthetic knees are fixed to the tibial component.

The present invention is directed to a constrained knee prosthesis with a rotating bearing. The knee prosthesis of the present invention is structured to facilitate implantation thereof. The present invention is further directed to a prosthetic knee implant set having a plurality of matched modular hinge post and meniscal component pairs.

SUMMARY OF THE INVENTION

The present invention provides an improved constrained knee prosthesis having a cannulated hinge post facilitating implantation of the knee prosthesis in a relatively minimally invasive procedure. The prosthetic knee implant set of the current invention includes a separately packaged femoral component, a separately packaged tibial component, and a third package containing a hinge post extension and the meniscal component. Packaging the individual components of a knee prosthesis in this fashion insures that the appropriate hinge post extension is readily available. A bearing box is interposed between the hinge post and the femoral component. The bearing box includes a hyperextension stop which cooperates with the hinge post to prevent hyperextension of the knee prosthesis. Various structures are utilized to prevent the disengagement of the constrained knee prosthesis of the present invention.

A prosthetic knee constructed in accordance with the present invention includes a femoral component having a pair of condyler surfaces and a hinge post rotatably connected to the femoral component between the condyler surfaces. The hinge post is cannulated and accommodates insertion of a hinge post extension shaft therein. The hinge post and hinge post extension include cooperating locking tapers for locking the hinge post extension to the hinge post. Additionally, the hinge post includes internal threads so that a set screw may be threaded therein to further hold the hinge post extension in place. In one exemplary embodiment, the proximal end of the hinge post extension is threaded to facilitate locking the hinge post extension to the hinge post. The tibial component includes a hinge post extension aperture into which the hinge post extension is seated. The meniscal component similarly includes an aperture to accommodate the hinge post and hinge post extension. The meniscal component of the current invention is free to rotate about the hinge post during flexion and extension of the knee joint.

Having a cannulated hinge post through which a hinge post extension may be anteriorly positioned and secured advantageously allows for a relatively minimally invasive knee replacement procedure.

The present invention advantageously provides a constrained prosthetic knee having a rotating bearing flush with the condyler surfaces of the femoral component.

Another advantage of the present invention is the packaging of the prosthesis components and specifically the packaging of the appropriate hinge post extension together with a meniscal component.

BRIEF DESCRIPTION OF THE DRAWINGS

The above-mentioned and other features and advantages of this invention, and the manner of attaining of them, will become more apparent and the invention itself will be better understood by reference to the following description of an embodiment of the invention taken in conjunction with the accompanying drawings, wherein:

FIG. 2A is a perspective view of a hinge post extension of the present invention;

FIG. 13 is a cutaway, exploded view of an alternative embodiment of the knee prosthesis of the present invention;

FIG. 14 is a cutaway view of an assembled knee prosthesis in accordance with the embodiment illustrated in FIG. 13;

FIG. 15 is a fragmentary, cutaway view of an alternative embodiment of the hinge post extension and tibial bushing of the present invention;

FIG. 16 is a fragmentary, cutaway view of the embodiment of FIG. 15 illustrating insertion of the hinge post extension into the tibial bushing;

FIG. 17 is a fragmentary, cutaway view of the embodiment of FIG. 15 illustrating the hinge post extension fully inserted into the tibial bushing;

FIG. 18 is an exploded view of an alternative embodiment of the knee prosthesis of the current invention;

FIG. 19 is a sectional view of a meniscal component in accordance with an alternative embodiment of the present invention;

FIG. 20 is an elevational view of a hinge post in accordance with an alternative embodiment of the present invention;

FIG. 21 is a top elevational view of a meniscal component in accordance with the present invention;

FIGS. 22, 23, 24, and 25 are bottom, back, front, and side elevational views thereof, respectfully;

FIG. 26 is a sectional view thereof;

FIG. 31 is a top elevational view of a tibial component in accordance with the present invention;

FIGS. 32, 33, 34, and 35 are bottom, back, front, and side elevational views thereof, respectively; and FIG. 36 is a sectional view thereof.

Figure 1:
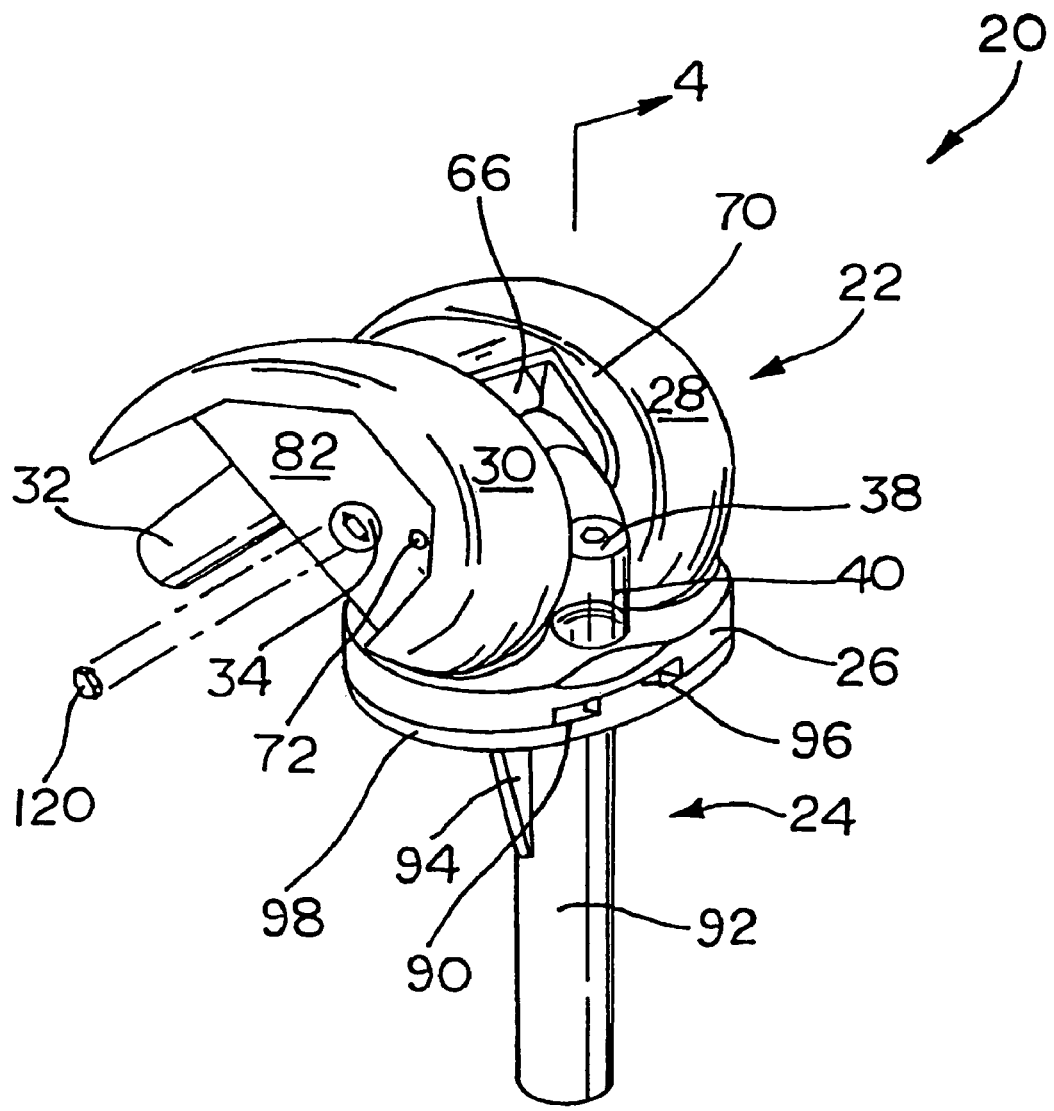
FIG. 1 is a perspective view of an assembled knee prosthesis in accordance with the present invention.

Corresponding reference characters indicate corresponding parts throughout the several views. Although the drawings represent embodiments of the invention, the drawings are not necessarily to scale and certain features may be exaggerated to better illustrate and explain the invention. The exemplifications set out herein illustrate embodiments of the invention, in alternative forms, and such exemplifications are not to be construed as limiting the scope of the invention in any manner.

DETAILED DESCRIPTION

Figure 2:
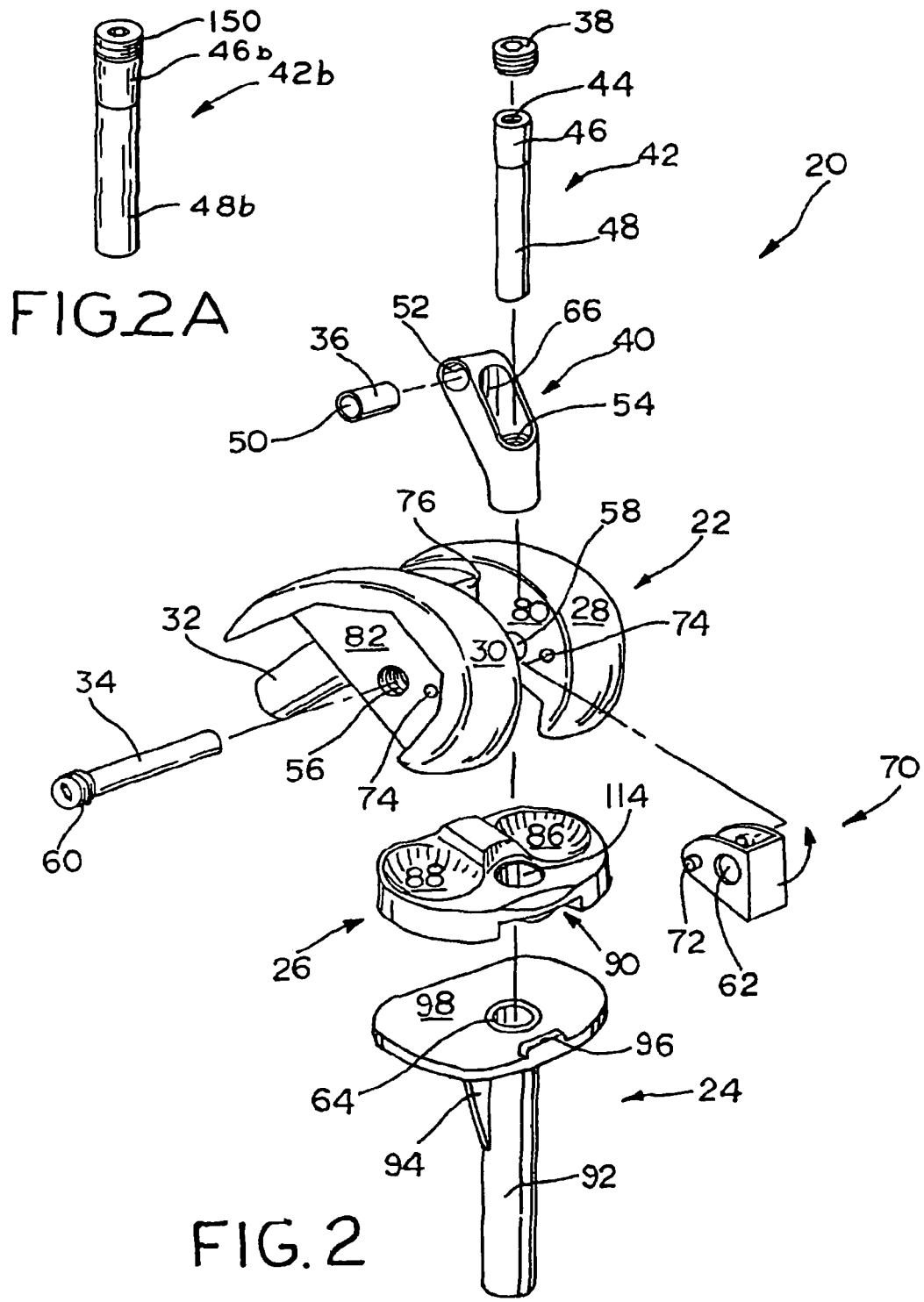
FIG. 2 is an exploded view thereof.
Figure 3:
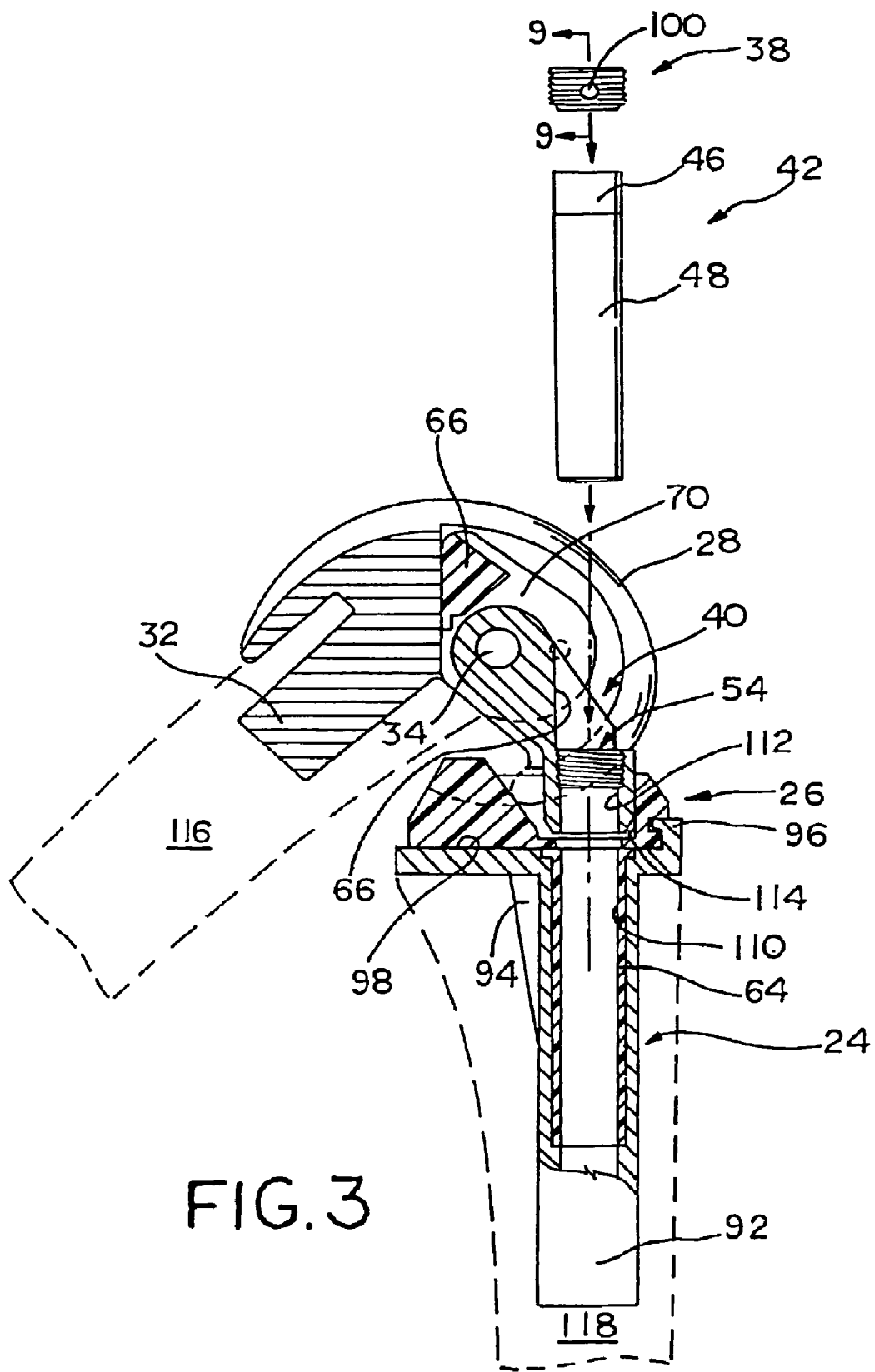
FIG. 3 is a cutaway, exploded view illustrating assembly of the knee prosthesis of the current invention including the anterior positioning of the hinge post extension into the hinge post.

Referring now to the drawings and particularly to FIG. 2, knee prosthesis 20 in accordance with the present invention is illustrated. Knee prosthesis 20 generally includes femoral component 22, tibial component 24, and meniscal component 26. Hinge post 40 is rotatably connected to femoral component 22 and includes elongate hinge post extension aperture 112 (FIGS. 3-6, 13, and 14). Elongate aperture 112 accommodates placement of hinge post extension 42 therein. Hinge post extension 42 thereafter traverses hinge post aperture 114 in meniscal component 26 and hinge post extension aperture 110 (FIGS. 3-6, 13 and 14) in tibial component 24. Elongate hinge post extension aperture 112 of hinge post 40 advantageously allows for anterior placement of hinge post extension 42 during surgical implantation of knee prosthesis 20 of the present invention.

Figure 4:
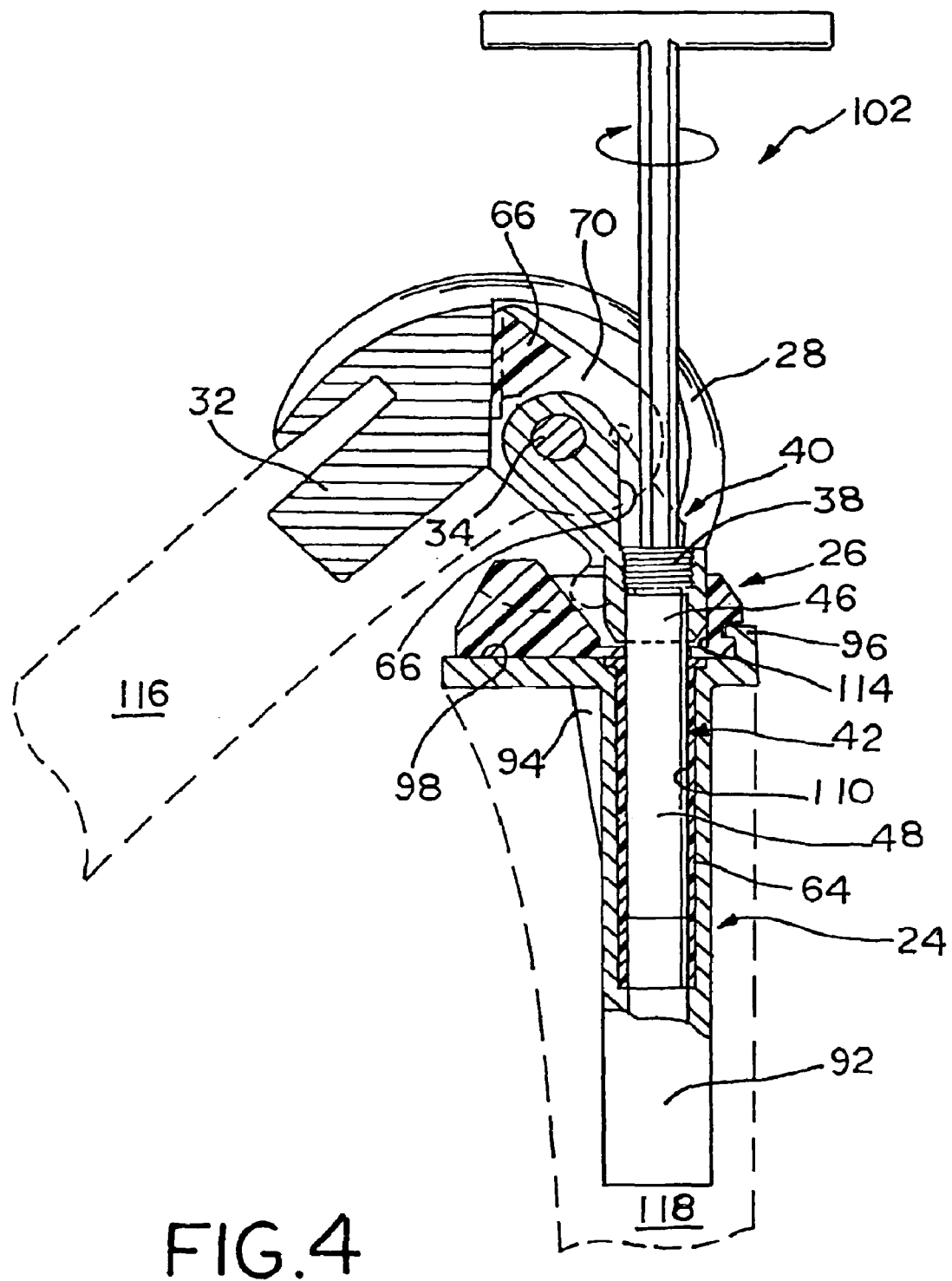
FIG. 4 is a cutaway view illustrating securement of the hinge plug (i.e., set screw) in the hinge post to facilitate locking of the hinge post extension therein.

As illustrated in FIG. 2, hinge post extension 42 includes locking taper 46 and cylindrical extension 48. Hinge post extension aperture 112 includes a mating locking taper to cooperate with locking taper 46 and lock hinge post extension 42 to hinge post 40. After positioning hinge post extension 42 through apertures 112, 114, and 110, hinge plug 38 may be threaded into hinge plug threads 54 in elongate aperture 112 of hinge post 40 (FIG. 4). Hinge plug 38 abuts the end of hinge post extension 42 and thereby facilitates locking of morse taper 46 in elongate aperture 112. In one exemplary embodiment, locking taper 46 comprises a two degree locking taper. In an alternative embodiment, the hinge post extension includes integral threads to facilitate locking of the hinge post extension to the hinge post. As illustrated in FIG. 2A, hinge post extension 42B includes locking taper 46B as well as threaded proximal end 150. If hinge post extension 42B is utilized, hinge plug 38 is unnecessary. When prosthetic knee 20 is assembled as illustrated in FIG. 1, condyler bearing surfaces 28, 30 abut bearing surfaces 86, 88 (see, e.g., FIG. 2) of meniscal component 26.

Figure 9:
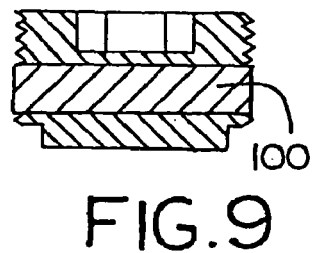
FIG. 9 is a sectional view of a hinge plug in accordance with the present invention.
Figure 7:
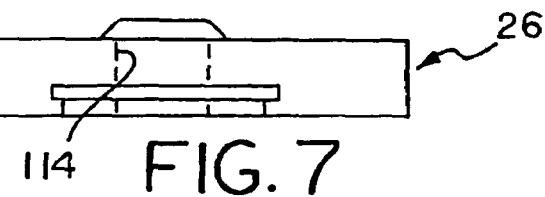
FIG. 7 is a front elevational view thereof.
Figure 8:
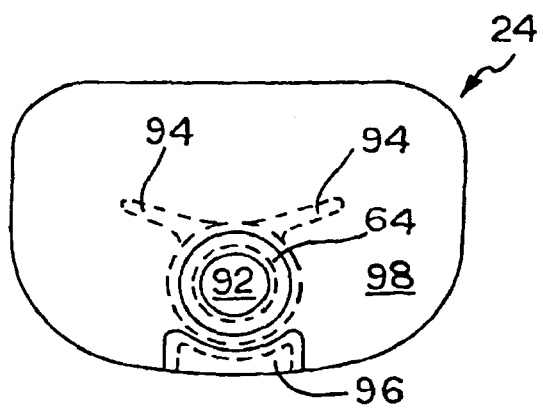
FIG. 8 is a top elevational view of a tibial component in accordance with the present invention.

Hinge post extension 42 is typically formed as a one-piece construction of an inert metal such, e.g., a cobalt-chromium alloy. Hinge post extension 42 may, however, be constructed of other bio-compatible metals or alloys, such as titanium. Throughout this document reference will be made to various components formed of a cobalt-chromium alloy. Any such component may also be constructed of other bio-compatible metals or alloys such as titanium, as is well-known. As illustrated in FIG. 4, hinge plug wrench 102 is utilized to thread hinge plug 38 into hinge plug threads 54 of hinge post 40. As illustrated in FIG. 9, hinge plug 38 includes locking material 100 to provide a locking connection between hinge plug 38 and hinge plug threads 54 in hinge post 40. Hinge plug 38 is, in one exemplary embodiment formed of a cobalt-chromium alloy. Locking material 100 comprises any suitable biocompatible polymer such as, e.g., ultra-high molecular weight polyethylene (UHMWPE).

As illustrated, e.g., in FIG. 2, femoral component 22 includes condyler bearing surfaces 28, 30 with bearing box wall 76 positioned therebetween. Femoral component 22 further includes external side walls 82, only one of which can be seen in FIG. 2. Condyler bearing surfaces 28, 30 are smooth and highly polished, generally spheroidally shaped and extend outwardly from external side walls 82, as is well known in the industry. Femoral component 22 further includes modular femoral stem 32 for insertion into femur 116 (FIGS. 3-5, 13, and 14), as is known in the art. Femoral component 22 further includes internal side walls 80, only one of which is illustrated in FIG. 2. Internal side walls 80 are substantially perpendicular to bearing box wall 76 and extend outwardly therefrom. Femoral component 22 is typically formed as a one-piece construction of an inert metal such as, e.g., a cobalt-chromium alloy.

Figure 10:
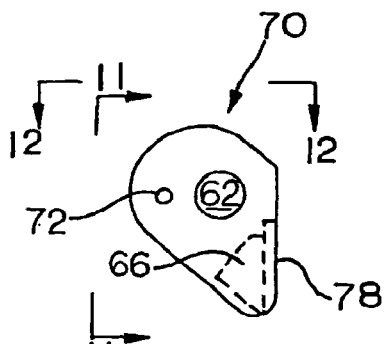
FIG. 10 is a side elevational view of a bearing box in accordance with the present invention.
Figure 11:
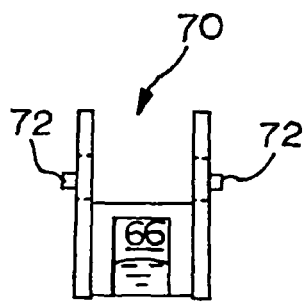
FIG. 11 is a front elevational view thereof.
Figure 12:
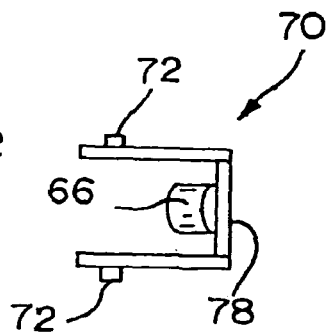
FIG. 12 is a top elevational view thereof.

Bearing box 70 is designed for placement between condyler bearing surfaces 28, 30 of femoral component 22 as illustrated, e.g., in FIG. 1. Bearing box 70 is further illustrated in FIGS. 10-12 and includes affixing protrusions 72, hinge pin aperture 62, hyperextension stop 66, and anti-rotation surface 78. As illustrated in FIG. 2, femoral component 22 includes affixing protrusion apertures 74 sized to receive affixing protrusions 72. FIG. 1 illustrates bearing box 70 operably positioned on femoral component 22, with anti-rotation surface 78 flush with bearing box wall 76 of femoral component 22, and affixing protrusions 72 received in affixing protrusion apertures 74. The abutting relationship of anti-rotation surface 78 with bearing box wall 76 discourages rotation of bearing box 70 about the longitudinal axis of affixing protrusions 72. When bearing box 70 is positioned on femoral component 22, hinge pin apertures 62 of bearing box 70 align with threaded hinge pin aperture 56 and hinge pin aperture 58 of femoral component 22. Bearing box 70 can be formed of any suitable plastic, such as, e.g., UHMWPE.

Hinge post 40 is rotatably connected to femoral component 22 via hinge pin 34. Hinge post 40 is placed between opposing walls of bearing box 70 and is positioned so that hinge pin aperture 52 is aligned with apertures 56, 58, and 62. The opposing walls of bearing box 70 thus act as a bearing surface between hinge post 40 and internal side walls 80 of femoral component 22. Prior to placement of hinge post 40 between opposing walls of bearing box 70, hinge pin sleeve 36 is operably positioned within hinge pin aperture 52 of hinge post 40. Hinge post 40 is formed from a cobalt-chromium alloy, while hinge pin sleeve 36 is formed from a suitable plastic, such as, e.g., UHMWPE. Hinge pin sleeve 36 acts as a bearing between hinge pin aperture 52 of hinge post 40 and hinge pin 34. Accordingly, hinge pin sleeve 36 includes hinge pin aperture 50 sized to accommodate hinge pin 34. After positioning hinge post 40 between the opposing walls of bearing box 70, hinge pin 34 is positioned through apertures 56, 62, 50, and 58. Hinge pin threads 60 are thereafter threadedly engaged in the threads of threaded hinge pin aperture 56 until the head of hinge pin 34 is flush with external side wall 82.

As illustrated in FIG. 1, hinge pin plug 120 is positioned within the hexagonal indentation of hinge pin 34 after installation of hinge pin 34 as described above. When positioned within the hexagonal indentation of hinge pin 34, hinge pin plug 120 is flush with the head of hinge pin 34. In use, hinge pin plug 120 substantially prohibits the entry of foreign materials into the hexagonal indentation of hinge pin 34. For example, hinge pin plug 120 substantially prohibits bone growth into the hexagonal indentation of hinge pin 34, as well as prohibiting positioning of bone cement therein. The above-described connection of hinge post 40 to femoral component 22 is performed prior to implantation of femoral component 22. Femoral component 22 is packaged and sold with bearing box 70, hinge post 40, hinge pin sleeve 36, hinge pin 34, and hinge pin plug 120 preassembled as described above, with the assembly preferably occurring in the manufacturing environment.

Pre-assembly of hinge post 40 to femoral component 22 eliminates a number of meticulous assembly steps (many of which were performed during implantation) which were required with constrained knees of the prior art. Furthermore, the assembly of hinge post 40 and femoral component 22 as described above facilitates replacement of various portions of knee prosthesis 20. Specifically, the threaded connection of hinge pin 34 to femoral component 22 allows for removal and replacement of various components of knee prosthesis 20 including, e.g., bearing box 70, hinge pin sleeve 36, and hinge post 40.

In use, femoral bone stock may abut external side walls 82 of femoral component 22 and extend to the underside of condyler bearing surfaces 28, 30. To remove hinge pin 34, a hole saw is utilized to remove a relatively small portion of femoral bone stock to provide access to hinge pin 34. Advantageously, femoral component 22 does not require extensive removal of femoral bone stock for implantation thereof (since bone stock can extend to the underside of condylar bearing surfaces 28, 30), and, furthermore, does not require removal of femoral component 22 to effect replacement of, e.g., hinge post 40, bearing box 70, or hinge pin sleeve 36. Upon accessing hinge pin 34 (e.g., utilizing a hole saw as described above), hinge pin plug 120 is removed, e.g., with a scalpel and forceps to provide access to the hexagonal indentation of hinge pin 34 so that a hexagonal wrench may be inserted therein to unthread hinge pin 34 from femoral component 22.

Knee prosthesis 20 includes a pair of hyperextension stop mechanisms. The first hyperextension stop comprises a portion of condylar bearing surfaces 28, 30 of increased radius of curvature as compared to the remaining condylar bearing surface. At three degrees of hyperextension this portion of increased radius of curvature will contact meniscal component 26 and act to retard further hyperextension. If hyperextension continues, the area of increased radius of curvature will cause femoral component 22 to lift away from meniscal component 26. The second hyperextension stop mechanism functions at four degrees of hyperextension to prohibit further hyperextension of knee prosthesis 20. The second hyperextension stop mechanism comprises hyperextension stop surface 66 of hinge post 40 and hyperextension stop 68 of bearing box 70. Hyperextension stop surface 66 comprises the concave back wall of cannulated hinge post 40 as illustrated, e.g., in FIGS. 2 and 3. Hyperextension stop 68 of bearing box 70 comprises a protrusion extending from the back wall of bearing box 70 opposite anti-rotation surface 78. Hyperextension stop 68 includes a convex outer surface as illustrated, e.g., in FIG. 12. Hyperextension stop surface 66 of hinge post 40 cooperates with hyperextension stop 68 of bearing box 70 to provide a hyperextension stop for knee prosthesis 20. Concave hyperextension stop surface 66 becomes flush with the convex outer surface of hyperextension stop 68 of bearing box 70 at four degrees of hyperextension to prevent further hyperextension of knee prosthesis 20.

Tibial component 24 is depicted in FIGS. 1-5, 8, 13, and 14. As illustrated, e.g., in FIG. 2, tibial component 24 includes tibial tray 98 connected to tibial stem 92. Stabilizing ribs 94 stabilize tibial tray 98 relative to tibial stem 92 and impede rotation of tibial component 24 in tibia 118 (see, e.g., FIG. 3). In one exemplary embodiment, tibial component 24 is formed from a cobalt-chromium alloy. Tibial component 24 further includes tibial bushing 64 positioned within hinge post extension aperture 110. Tibial bushing 64 is formed of plastic, such as, e.g., UHMWPE and provides a bearing surface between hinge post extension 42 and hinge post extension aperture 110 of tibial component 24. As described above, meniscal component 26 comprises a rotating bearing, and, thus, hinge post extension 42 will rotate relative to tibial component 24. Tibial bushing 64 facilitates this rotation of hinge post extension 42.

Tibial component 24 further includes rotation protrusion 96. As illustrated, e.g., in FIG. 3, rotation protrusion 96 protrudes upwardly from tibial tray 98 of tibial component 24 and further extends in a plane substantially parallel to tibial tray 98. Rotation protrusion 96 cooperates with cutout 90 of meniscal component 26 to guide rotation of meniscal component 26 about hinge post extension 42, as further described hereinbelow. FIGS. 31-36 illustrate an alternative embodiment tibial component 24b. As illustrated, e.g., in FIG. 35, tibial component 24b includes a pair of rotation protrusions, i.e., anterior rotation protrusion 180, and posterior rotation protrusion 182. Rotation protrusions 180, 182 protrude upwardly from tibial tray 98b of tibial component 24b and further extend in a plane substantially parallel to tibial tray 98b. Rotation protrusions 180, 182 cooperate with anterior cutout 160, and posterior cutout 162 of meniscal component 26b, respectively (see, e.g., FIGS. 21-26) to guide rotation of meniscal component 26b about the hinge post extension, as further described hereinbelow.

One embodiment of meniscal component 26 is illustrated in FIGS. 1-7, 13, and 14. Meniscal component 26 is formed from a suitable plastic such as, e.g., UHMWPE and provides a rotating bearing surface between femoral component 22 and tibial component 24. Meniscal component 26 includes bearing surfaces 86, 88 which contact condylar bearing surfaces 28, 30 of femoral component 22 during movement of knee prosthesis 20. As described above, meniscal component 26 further includes hinge post aperture 114 accommodating passage of hinge post 40 and, consequently, hinge post extension 42 therethrough. Meniscal component 26 is operable to rotate about the longitudinal axis of hinge post extension 42 to form a rotating bearing.

Meniscal components of varying heights may be constructed in accordance with the present invention. In one advantageous aspect of the present invention, meniscal component 26 is packaged for sale and use together with hinge post extension 42 to facilitate component choice and, in one embodiment, to ensure proper extension of hinge post extension 42 into tibial component 24. The extension of hinge post extension 42 into tibial component 24 functions to prevent separation of knee prosthesis 20 after implantation thereof. As is known in the art, the femoral component of a knee prosthesis may, in some situations, move relative to and away from the tibial component in a direction parallel to the longitudinal axis of the hinge post extension. With this in mind, hinge post extension 42 is made to be of sufficient length to be retained within tibial component 24 even in situations in which femoral component 22 moves as described immediately supra. In one exemplary embodiment, hinge post extension 42 extends four centimeters into hinge post extension aperture 110 in tibial component 24.

Meniscal component 26 includes cutout 90 which cooperates with rotation protrusion 96 of tibial component 24 to guide rotation of meniscal component 26 and to resist lifting of meniscal component 26 from tibial tray 98 of tibial component 24. As illustrated, e.g., in FIG. 3, cutout 90 accommodates the portion (i.e., lip) of rotation protrusion 96 extending in a plane substantially parallel to the plane containing tibial tray 98, with a portion (i.e., lip) of meniscal component 26 being positioned between rotation protrusion 96 and tibial tray 98 in a direction substantially perpendicular to the plane containing tibial tray 98. This configuration functions to discourage displacement of meniscal component 26 away from tibial tray 98 in a direction parallel to the longitudinal axis of hinge post extension 42. Furthermore, rotation protrusion 96 acts against the back of cutout 90 to limit rotation of meniscal component 26 about the longitudinal axis of hinge post extension 42.

Meniscal component 26b illustrated in FIGS. 21-26, includes a pair of cutouts 160, 162 for cooperation with rotation protrusions 180, 182 of tibial component 24b (see, e.g., FIGS. 31-36) to guide rotation of meniscal component 26b and to resist lifting of meniscal component 26b from tibial tray 98b of tibial component 24b. As illustrated, e.g., in FIG. 26, meniscal component 26b includes anterior cutout 160 as well as posterior cutout 162, with anterior capture protrusion 170 and posterior capture protrusion 172 respectively extending therefrom. As illustrated in FIGS. 22 and 26, meniscal component 26b further includes channel 164 sized to accommodate posterior rotation protrusion 182 of tibial component 24b as will be further described hereinbelow.

As illustrated in FIGS. 27-30, tibial component 24b includes a pair of rotation protrusions, i.e., anterior rotation protrusion 180 and posterior rotation protrusion 182. As illustrated, e.g., in FIG. 30, anterior cutout 160 and posterior cutout 162 in meniscal component 26b respectively accommodate anterior capture protrusion 170 and posterior capture protrusion 172 formed in tibial component 26b. Specifically, cutouts 160, 162 accommodate the portion, i.e., lip of rotation protrusions 180, 182 extending in a plane substantially parallel to the plane containing tibial tray 98b, with a portion, i.e., lip of meniscal component 26b being positioned between the portions of rotation protrusions 180, 182 extending in a plane substantially parallel to the plane containing tibial tray 98, and tibial tray 98 when meniscal component 26b is operably positioned atop tibial tray 98b as illustrated, e.g., in FIG. 30. The cooperation of rotation protrusions 180, 182 with capture protrusions 170, 172, as illustrated, e.g., in FIG. 30 functions to discourage displacement of meniscal component 26b away from tibial tray 98b in a direction perpendicular to tibial tray 98b when the knee prosthesis of the current invention is operably assembled as illustrated, e.g., in FIG. 1. Furthermore, cutouts 160, 162 are sized whereby rotation protrusions 180, 182 cooperate therewith to limit rotation of meniscal component 26b about an axis generally perpendicular to tibial tray 98b of tibial component 24b. In one exemplary embodiment, meniscal component 26b is capable of a total of sixty degrees of rotation from one extreme to the other.

Figures 27, 28:
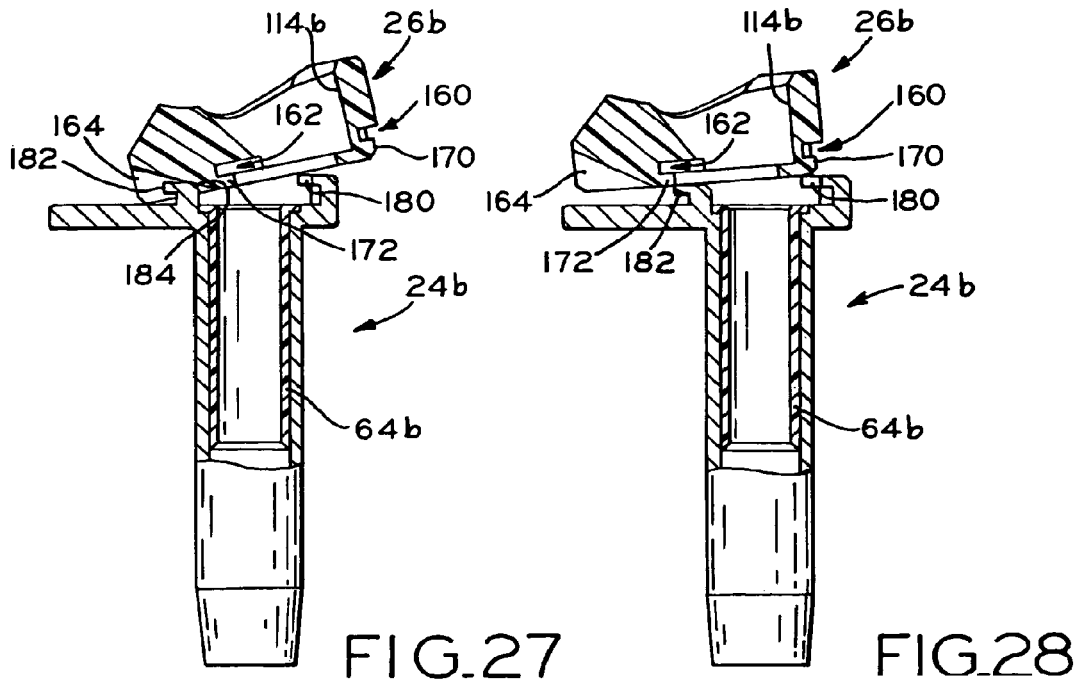
FIG. 27 is a sectional view illustrating initial placement of a meniscal component of the present invention on a tibial component of the present invention.
FIGS. 28-30 are sectional views progressively illustrating placement of a meniscal component of the present invention on a tibial component of the present invention, whereby the meniscal component is operable to rotate relative to the tibial component when operably positioned thereon, but is constrained from movement in an axial direction relative to the tibial stem, i.e., the meniscal component will not lift away from the tibial component.
Figures 29, 30:
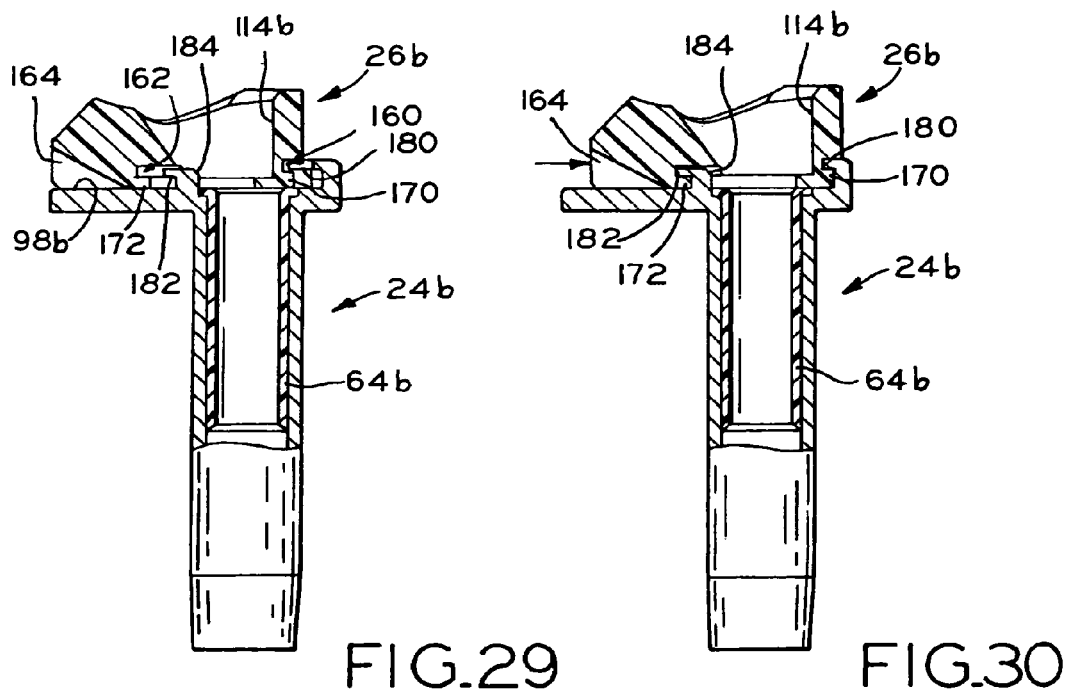

FIGS. 27-30 progressively illustrate movement of meniscal component 26b relative to tibial component 24b to achieve proper positioning of meniscal component 26b atop tibial tray 98b of meniscal component 24b. As illustrated in FIG. 27, posterior rotation protrusion 182 of tibial component 24b is positioned within channel 164 formed in meniscal component 26b, with meniscal component 26b resting atop rotation protrusion 180. Meniscal component 26b is thereafter moved posteriorly as illustrated in FIG. 28 until capture protrusions 170, 172 no longer rest atop rotation protrusions 180, 182, and meniscal component 26b is moved into contact with tibial tray 98b as illustrated in FIG. 29. Meniscal component 26b is subsequently moved anteriorly so that capture protrusions 170, 172 engage rotation protrusions 180, 182, respectively, to prevent movement of meniscal component 26b in a direction generally perpendicular to the plane containing tibial tray 98b, as illustrated in FIG. 30. As illustrated in FIG. 27, posterior rotation protrusion 82 includes bevel 184 to facilitate posterior movement of meniscal component 26b. Once meniscal component 26b is moved into the position illustrated in FIG. 30, hinge post extension 42 may be operably positioned within the tibial component as illustrated, e.g., in FIG. 4.

Figure 5:
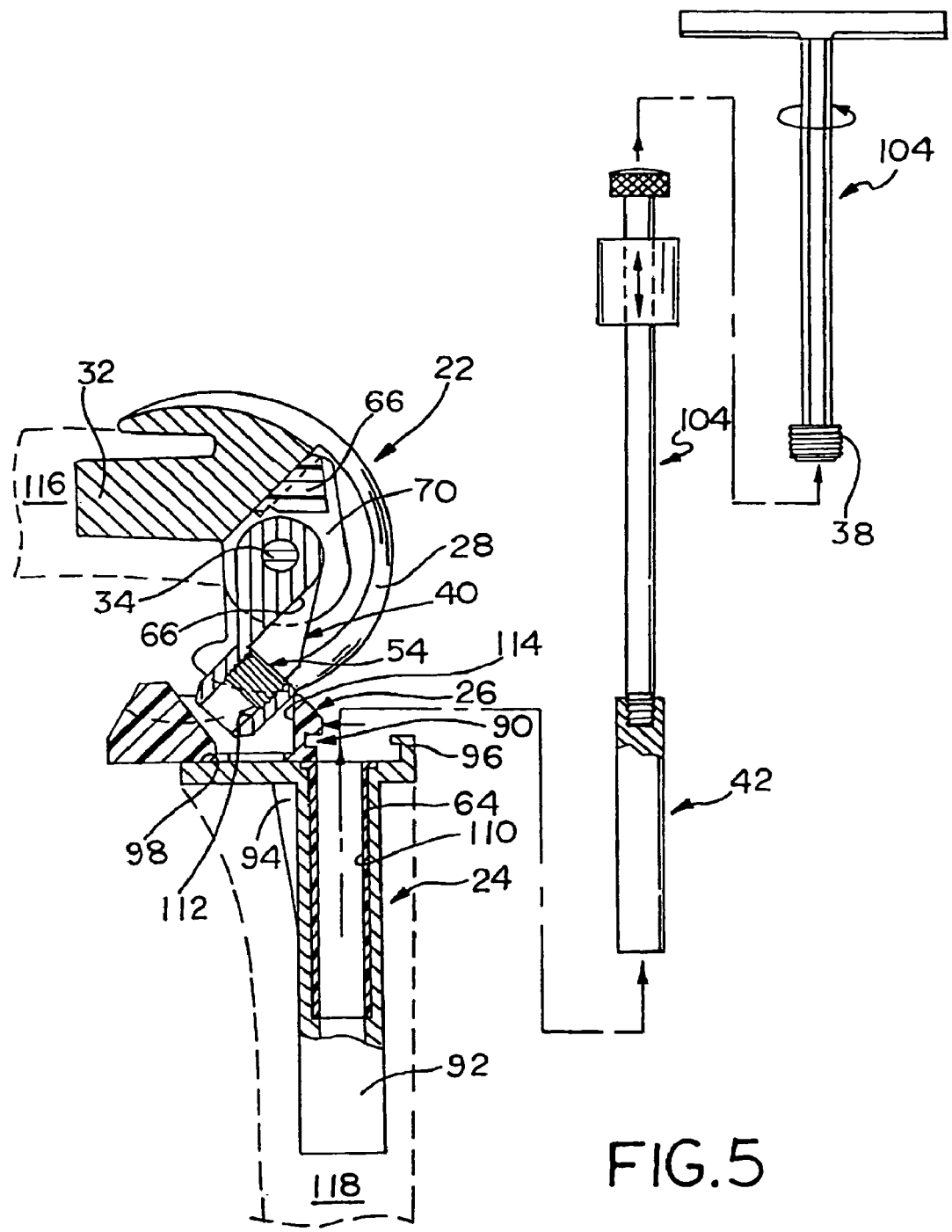
FIG. 5 is a cutaway, exploded view illustrating removal of the hinge post extension.
Figure 6:
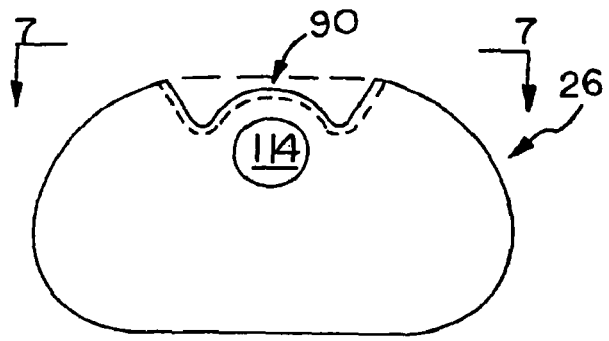
FIG. 6 is a bottom elevational view of the meniscal component of the present invention.

Positioning of meniscal component 26b as described above in conjunction with FIGS. 27-30, may be effected in vivo with femoral component 22 in place, i.e., implanted in femur 116 as illustrated e.g., in FIG. 5. If meniscal component 26b is positioned with femoral component 22 in place, the steps described above will occur with condylar bearing surfaces 28-30 resting atop bearing surfaces 86b, 88d of meniscal component 26b, and with hinge post 40 positioned within hinge post aperture 114b of meniscal component 26b. As meniscal component 26b is moved relative to tibial component 24b as illustrated in FIGS. 27-30, hinge post 40 will rotate relative to femoral component 22 and move with meniscal component 26b.

As illustrated in FIG. 5, meniscal component 26 may be slid out from between tibial component 24 and femoral component 22 when hinge post extension 42 has been removed from knee prosthesis 20. As illustrated, hinge post aperture 114 is sized to allow rotation of hinge post 40 so that meniscal component 26 may be slid out from its position between femoral component 22 and tibial component 24. Similarly, meniscal component 26b may be removed from position between tibial component 24b and the femoral component when hinge post extension 42 has been removed from knee prosthesis 20. If meniscal component 26b and tibial component 24b are utilized, meniscal component 26b is removed by reversing the steps utilized to position meniscal component 26b atop tibial component 24b described above in conjunction with FIGS. 27-30. This allows for replacement of an implanted meniscal component 26 without requiring removal of hinge post 40.

FIG. 5 illustrates removal of hinge post extension 42 to accommodate replacement of meniscal component 26. As illustrated, hinge plug wrench 102 engages hinge plug 38 for removal thereof. After removal of hinge plug 38, slap hammer 104 is threadedly engaged with threaded aperture 44 in hinge post extension 42. Slap hammer 104 may then be utilized to unlock the engagement of locking taper 46 in elongate hinge post extension aperture 112 so that hinge post extension 42 may be removed. If hinge post extension 42b illustrated in FIG. 2a is utilized, wrench 102 will be utilized to rotate hinge post extension 42b to cause threaded proximal end 150 thereof to retreat from hinge plug threads 54 in hinge post 40, thereby releasing engagement of locking taper 46b in elongate hinge post extension aperture 112 and allowing for removal of hinge post extension 42b.

FIGS. 13 and 14 illustrate a further alternative embodiment of the knee prosthesis of the current invention. This alternative embodiment utilizes hinge post extension 42a having locking taper 46a, cylindrical extension 48a, and flange 106. In this embodiment, a locking instrument may be utilized to apply force atop hinge post extension 42a so that locking taper 46a is seated in elongate hinge post extension aperture 112 and locked therein. Flange 106 may be utilized to facilitate removal of hinge post extension 42a. As illustrated in FIG. 13, set screw 108 may be utilized as a secondary lock for hinge post extension 42a.

FIGS. 15, 16 and 17 illustrate another alternative embodiment of the hinge post extension and tibial bushing of the present invention. In this embodiment, tibial component 24a includes annular tibial bushing expansion groove 122 formed in hinge post extension aperture 110. Tibial bushing 64a includes retaining flange 130 positioned within annular tibial bushing expansion groove 122. FIG. 15 illustrates insertion of cylindrical extension 48b of the hinge post extension into tibial bushing 64a positioned within tibial component 24a. As cylindrical extension 48b proceeds into tibial bushing 64a, bevel 126 contacts annular locking protrusion 128 of tibial bushing 64a and causes outward movement of retaining flange 130 as illustrated in FIG. 16 to allow cylindrical extension 48b to proceed to its seated position as illustrated in FIG. 17. Annular tibial bushing expansion groove 122 is sized to allow radial expansion of retaining flange 130 to accommodate placement of cylindrical extension 48b within tibial bushing 64a. In the fully seated position (FIG. 17) cylindrical extension 48b is locked in place by the engagement of annular locking protrusion 128 in annular locking groove 124. Furthermore, retaining flange 130 cooperates with annular tibial bushing expansion groove 122 to prohibit axial displacement of tibial bushing 64a and, consequently, cylindrical extension 48b. In this embodiment, the femoral component is retained in abutting relationship to the meniscal component and lift off of the femoral component is substantially prohibited. Tibial bushing 64a is, in one exemplary embodiment, formed of UHMWPE.

FIGS. 18 and 19 illustrate yet another alternative embodiment of the knee prosthesis of the current invention. In this embodiment, locking clip 134 is utilized to retain the position of hinge post 40b within hinge post aperture 114 of meniscal component 26a. Hinge post 40b is rotatably attached to femoral component 22 utilizing hinge pin 34 as described above. In this embodiment, hinge post 40b includes locking clip grooves 132, and meniscal component 26a includes locking clip apertures 136. Upon positioning of hinge post 40b within hinge post aperture 114, locking clip 134 is positioned as illustrated in FIG. 19 with the prongs of locking clip 134 being inserted into locking clip apertures 136 of meniscal component 26a. As illustrated in FIG. 19, locking clip 134 engages locking clip grooves 132 to retain hinge post 40b within hinge post aperture 114 of meniscal component 26a. In this embodiment, lift off of femoral component 22 is prohibited by the engagement of hinge post 40b with meniscal component 26a. This embodiment of the knee prosthesis of the current invention may further utilize a meniscal component cutout together with a rotation protrusion on the tibial component to resist lifting of the meniscal component from the tibial tray as described above.

FIG. 20 illustrates a further alternative embodiment of the hinge post of the present invention. Hinge post 40c illustrated in FIG. 20 includes reinforcing material 138 to strengthen hinge post 40c.

While this invention has been described as a prosthetic knee with a rotating bearing, it is contemplated that various aspects of the present invention, including, e.g., the cannulated hinge post will be utilized with a prosthetic knee having a fixed bearing.

While this invention has been described as having exemplary designs, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of implanting a knee prosthesis in a tibia and a femur, the method comprising:
   attaching to the femur a femoral component comprising a condylar bearing surface and a hinge post rotatably connected to the femoral component about an axis of rotation, the hinge post including a tubular portion with an elongate aperture passing entirely therethrough, the elongate aperture defining a first end, a second end and an axis transverse to the axis of rotation:

attaching to the tibia a tibial component having a tibial tray, the tibial tray having a superior surface, said attaching step done so that the superior surface is exposed;

after said attaching steps, sliding, along a generally anteroposterior path between the condylar bearing surface and the superior surface of the tibial tray, a meniscal component having a meniscal bearing surface for cooperation with the condylar bearing surface of the femoral component, the meniscal component having an inferior surface opposite the meniscal bearing surface, the inferior surface adapted to slide along the superior surface of the tibial tray, the meniscal component having a meniscal aperture sized to receive the tubular portion of the hinge post and to allow rotation of the hinge post about the axis of rotation when the hinge post is received within the meniscal aperture;

during said step of sliding the meniscal component and with the hinge post rotatably connected to the femoral component, positioning the tubular portion of the hinge post within the meniscal aperture; and coupling the hinge post to the tibial component.

2. The method of claim 1, further comprising, during the step of sliding the meniscal component:

contacting the condylar bearing surface of the femoral component with the meniscal bearing surface of the meniscal component; and during the step of contacting the condylar bearing surface with the meniscal bearing surface, contacting the superior surface of the tibial component with the inferior surface of the meniscal component, whereby the meniscal component contacts both the tibial component and the femoral component during said step of sliding the meniscal component.

3. The method of claim 1, wherein the meniscal aperture defines an aperture wall forming a closed profile in a transverse plane generally parallel to the tibial tray.

4. The method of claim 1, wherein said step of sliding the meniscal component comprises sliding a cutout formed in the inferior surface of the meniscal component into contact with a superiorly extending protrusion formed on an anterior portion of the superior surface of the tibial tray.

5. The method of claim 1, wherein said step of coupling the hinge post to the tibial component comprises:

articulating the femoral component with respect to the tibial component to place the knee prosthesis in a flexion orientation, said step of articulating the femoral component exposing the first end of the elongate aperture of the hinge post; and after said steps of sliding the meniscal component and articulating the femoral component, passing a hinge post extension through the first end of the elongate aperture and through the second end of the elongate aperture, the hinge post extension extending past the inferior surface of the meniscal component and into engagement with the tibial component.

6. The method of claim 5, wherein the tibial component includes a tibial stem adapted to be implanted into the tibia, the tibial tray connected to the tibial stem, said step of passing the hinge post extension through the elongate aperture of the hinge post further comprising:

passing the hinge post extension through the tibial tray of the tibial component and into a bore formed in the tibial stem.

7. The method of claim 5, further comprising:

securing the hinge post extension within the elongate aperture of the hinge post.

8. The method of claim 7, wherein said step of securing the hinge post extension comprises engaging a male taper positioned on the hinge post extension with a female taper positioned in the elongate aperture of the hinge post proximate the first end.

9. The method of claim 8, wherein said step of securing the hinge post extension further comprises:

threadably engaging a hinge plug in a threaded superior end of the tubular portion proximate the first end, the hinge plug abutting an end of the hinge post extension when the hinge plug is threadably engaged with the tubular portion; and after the hinge plug abuts the end of the hinge post extension, forcing the male taper into locking engagement with the cooperating female taper by further threadably engaging the hinge plug with the threaded superior end of the tubular portion.

10. The method of claim 8, wherein said step of securing the hinge post extension further comprises:

threadably engaging a set screw in a threaded aperture formed in a wall of the tubular portion; and impinging the hinge post extension with the set screw when the hinge post extension is received within the elongate aperture of the hinge post.

11. The method of claim 1, wherein the meniscal component comprises a first meniscal component, the method further comprising:

removing the first meniscal component by sliding the first meniscal component along a generally anteroposterior path between the condylar bearing surface and the superior surface of the tibial tray, the anteroposterior path of said step of removing the meniscal component substantially opposite the anteroposterior path of said step of sliding the meniscal component; and sliding a second meniscal component, different from the first meniscal component, along a generally anteroposterior path between the condylar bearing surface of the femoral component and the superior surface of the tibial tray, wherein said steps of removing the first meniscal component and sliding the second meniscal component are performed with the hinge post rotatably connected to the femoral component.

12. The method of claim 11, further comprising, during the step of sliding the second meniscal component:

contacting the condylar bearing surface of the femoral component with a meniscal bearing surface of the second meniscal component; and during the step of contacting the condylar bearing surface of the femoral component with the meniscal bearing surface of the second meniscal component, contacting the superior surface of the tibial component with an inferior surface of the second meniscal component, whereby the second meniscal component contacts both the tibial component and the femoral component during said step of sliding the second meniscal component.

13. The method of claim 1, wherein the femoral component further comprises:

a bearing box including a hyperextension stop, the bearing box connected to the femoral component so that the bearing box is interposed between the hinge post and the femoral component, the hinge post having a hyperextension stop surface, the hyperextension stop sized to contact the hyperextension stop surface at a predetermined point of hyperextension to prevent further hyperextension of the knee prosthesis.

14. The method of claim 13, wherein the predetermined point of hyperextension comprises four degrees of hyperextension of the knee prosthesis.

15. The method of claim 1, wherein the femoral component further comprises:
a hinge pin having a longitudinal axis, the hinge pin hingedly coupling the hinge post to the femoral component
so that the hinge post is rotatable about the longitudinal axis of the hinge pin.

16. The method of claim 15 wherein the femoral component further comprises a hinge pin plug positioned within an indentation formed in a first end of the hinge pin, so that the hinge pin plug is flush with the first end of the hinge pin.

17. The method of claim 16, wherein the hinge pin plug is formed from an ultra-high molecular weight polyethylene.

18. A method of implanting a knee prosthesis in a tibia and a femur, the method comprising:
attaching to the femur a femoral component comprising a condylar bearing surface and a hinge post rotatably connected to the femoral component about an axis of rotation, the hinge post including a tubular portion with an elongate aperture passing entirely therethrough, the elongate aperture defining a first end, a second end and an axis transverse to the axis of rotation;
attaching to the tibia a tibial component having a tibial tray, the tibial tray having a superior surface, said attaching step done so that the superior surface is exposed;
after said attaching steps, sliding, along a generally anteroposterior path between the condylar bearing surface and the superior surface of the tibial tray, a meniscal component having a meniscal bearing surface for cooperating with the condylar bearing surface of the femoral component, the meniscal component having an inferior surface opposite the meniscal bearing surface, the inferior surface adapted to slide along the superior surface of the tibial tray, the meniscal component having a meniscal aperture sized to receive the tubular portion of the hinge post and to allow rotation of the hinge post about the axis of rotation when the hinge post is received within the meniscal aperture;
during said step of sliding the meniscal component and with the hinge post rotatably connected to the femoral component, positioning the tubular portion of the hinge post within the meniscal aperture;
articulating the femoral component with respect to the tibial component to place the knee prosthesis in a flexion orientation, said step of articulating the femoral component exposing the elongate aperture of the hinge post;
after said attaching steps of sliding the meniscal component and articulating the femoral component, passing a hinge post extension through the elongate aperture of the hinge post, past the inferior surface of the meniscal component, and into engagement with the tibial component.

19. The method of claim 18, further comprising, during the step of sliding the meniscal component:
contacting the condylar bearing surface of the femoral component with the meniscal bearing surface of the meniscal component; and
during the step of contacting the condylar bearing surface with the meniscal bearing surface, contacting the superior surface of the tibial component with the inferior surface of the meniscal component, whereby the meniscal component contacts both the tibial component and the femoral component during said step of sliding the meniscal component.

20. The method of claim 18, wherein said tibial component includes a tibial stem adapted to be implanted into the tibia, the tibial tray connected to the tibial stem, said step of passing the hinge post extension through the elongate aperture of the hinge post further comprises:
passing the hinge post extension through the tibial tray of the tibial component and into a bore formed in the tibial stem.

21. The method of claim 18, further comprising:
securing the hinge post extension within the elongate aperture of the hinge post using a means for securing.

22. The method of claim 18, wherein the femoral component further comprises:
means for preventing hyperextension in the knee prosthesis at a predetermined point of hyperextension.

23. The method of claim 18, wherein the femoral component further comprises:
means for rotatably connecting the hinge post to the femoral component so that an axis of rotation of the femoral component is coincident with the axis of rotation of the hinge post when the femoral component is coupled to the hinge post.

24. A method of implanting a knee prosthesis in a tibia and a femur, the knee prosthesis comprising:
a femoral component comprising a condylar bearing surface, a hinge post rotatably connected to the femoral component about an axis of rotation, the hinge post including a tubular portion with an elongate aperture passing entirely therethrough, the elongate aperture defining a first end, a second end and an axis transverse to the axis of rotation, a hinge pin having a longitudinal axis, the hinge pin hingedly coupling the femoral component with the hinge post by engaging within a transverse bore formed in the femoral component, the transverse bore having an axis coincident with the axis of rotation of the hinge post when the femoral component is coupled with the hinge post, so that the hinge post is hingedly rotatable about the longitudinal axis of the hinge pin;
a tibial component having a tibial tray, the tibial tray having a superior surface; and
a meniscal component having a meniscal bearing surface for cooperation with the condylar bearing surface of the femoral component, the meniscal component having an inferior surface opposite the meniscal bearing surface, the inferior surface adapted to slide along the superior surface of the tibial tray, the meniscal component having a meniscal aperture sized to receive the tubular portion of the hinge post and to allow rotation of the hinge post about the axis of rotation when the hinge post is received within the meniscal aperture;

the method comprising:
sliding the meniscal component along a generally anteroposterior path between the condylar bearing surface and the superior surface of the tibial tray;
during said step of sliding the meniscal component positioning the tubular portion of the hinge post within the meniscal aperture; and
coupling the hinge post to the tibial component.

25. The method of claim 1, wherein the meniscal component includes a locking clip aperture and the hinge post includes a locking clip groove, the method further comprising:

traversing said locking clip aperture of the meniscal component with a locking clip; and subsequent to said traversing step, engaging the locking clip groove of the hinge post with the locking clip to retain the hinge post within the meniscal aperture.

* * * * *